United States Patent
Saraliev et al.

(10) Patent No.: US 10,524,870 B2
(45) Date of Patent: Jan. 7, 2020

(54) MECHANICAL JOINTS, AND RELATED SYSTEMS AND METHODS

(71) Applicant: INTUITIVE SURGICAL OPERATIONS, INC., Sunnyvale, CA (US)

(72) Inventors: Daniel P. Saraliev, Soquel, CA (US); Matthew R. Williams, Walnut Creek, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 581 days.

(21) Appl. No.: 15/118,814

(22) PCT Filed: Feb. 20, 2015

(86) PCT No.: PCT/US2015/016854
§ 371 (c)(1),
(2) Date: Aug. 12, 2016

(87) PCT Pub. No.: WO2015/127231
PCT Pub. Date: Aug. 27, 2015

(65) Prior Publication Data
US 2017/0215977 A1    Aug. 3, 2017

Related U.S. Application Data

(60) Provisional application No. 61/943,084, filed on Feb. 21, 2014.

(51) Int. Cl.
*A61B 34/37*    (2016.01)
*A61B 90/00*    (2016.01)
(Continued)

(52) U.S. Cl.
CPC .............. *A61B 34/37* (2016.02); *A61B 34/71* (2016.02); *A61B 90/361* (2016.02); *A61B 90/37* (2016.02);
(Continued)

(58) Field of Classification Search
CPC ....... A61B 34/37; A61B 34/71; A61B 90/361; A61B 90/37; A61B 2034/306; A61B 2034/305; A61B 2034/302
(Continued)

(56) References Cited

U.S. PATENT DOCUMENTS 7,320,700 B2 *  1/2008  Cooper .................. A61B 1/008
                                                                  606/205
7,608,083 B2    10/2009  Lee et al.
(Continued)

FOREIGN PATENT DOCUMENTS

CN    102791218 A    11/2012
EP    3085324 A1     10/2016
(Continued)

OTHER PUBLICATIONS

International Search Report and Written Opinion for Application No. PCT/US15/16854, dated May 27, 2015, 17 pages.
(Continued)

*Primary Examiner* — Brian T Gedeon
(74) *Attorney, Agent, or Firm* — Jones Robb, PLLC

(57) ABSTRACT

A surgical instrument may comprise a shaft comprising a wrist at a first end, an end effector coupled to the wrist, and an actuation element that extends along the shaft and the wrist. The actuation element may follow a twisted path along at least a portion of the wrist. The twisted path may have an angular extent of less than 360 degrees along an entire length of the wrist. A method of configuring a surgical instrument wrist is also contemplated, as well as a support
(Continued)

structure for an actuation element of a surgical instrument. The support structure may comprise at least one passage defining a twisted path about a longitudinal axis of the support structure. The passage may have an angular extent of less than 360 degrees from a first end of the passage to a second end of the passage.

33 Claims, 19 Drawing Sheets

(51) Int. Cl.
  *A61B 34/00* (2016.01)
  *A61B 34/30* (2016.01)
(52) U.S. Cl.
  CPC ... *A61B 2034/302* (2016.02); *A61B 2034/305* (2016.02); *A61B 2034/306* (2016.02)
(58) Field of Classification Search
  USPC .......................................................... 600/1
  See application file for complete search history.

(56) References Cited

U.S. PATENT DOCUMENTS

| | | | |
|---|---|---|---|
| 7,819,884 B2* | 10/2010 | Lee | A61B 34/20 600/114 |
| 7,942,868 B2 | 5/2011 | Cooper | |
| 8,545,515 B2 | 10/2013 | Prisco et al. | |
| 2006/0094931 A1 | 5/2006 | Danitz et al. | |
| 2007/0112355 A1 | 5/2007 | Salahieh et al. | |
| 2008/0065105 A1 | 3/2008 | Larkin et al. | |
| 2009/0191974 A1 | 7/2009 | Weissenbock et al. | |
| 2011/0196419 A1 | 8/2011 | Cooper | |
| 2012/0215220 A1 | 8/2012 | Manzo et al. | |
| 2012/0277762 A1 | 11/2012 | Lathrop et al. | |
| 2012/0310221 A1 | 12/2012 | Durant et al. | |
| 2012/0310254 A1 | 12/2012 | Manzo et al. | |
| 2013/0012928 A1 | 1/2013 | Cooper et al. | |
| 2013/0340559 A1 | 12/2013 | Danitz et al. | |

FOREIGN PATENT DOCUMENTS

| | | |
|---|---|---|
| JP | 2004337994 A | 12/2004 |
| JP | 2013518665 A | 5/2013 |
| WO | WO-2011097095 A1 | 8/2011 |
| WO | WO-2015127250 A1 | 8/2015 |

OTHER PUBLICATIONS

Salle D., et al., "Surgery Grippers for Minimally Invasive Heart Surgery," Proceeding of IEEE International Conference on Intelligent Manipulation and Grasping (IMG 04), Jul. 2004, 8 pages.

Extended European Search Report for Application No. 15752254.1, dated Jun. 9, 2017, 10 pages.

Office Action dated Jul. 27, 2018 for Chinese Application No. 201580009399.2 filed Feb. 20, 2015, 24 pages.

\* cited by examiner

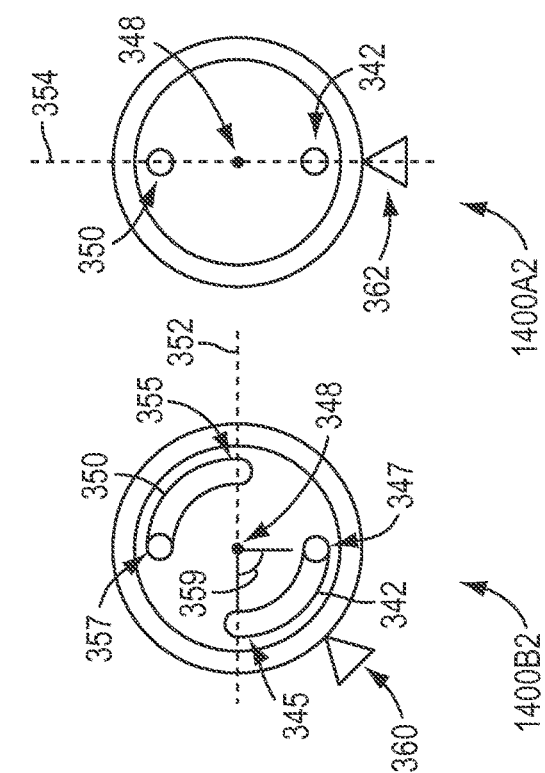
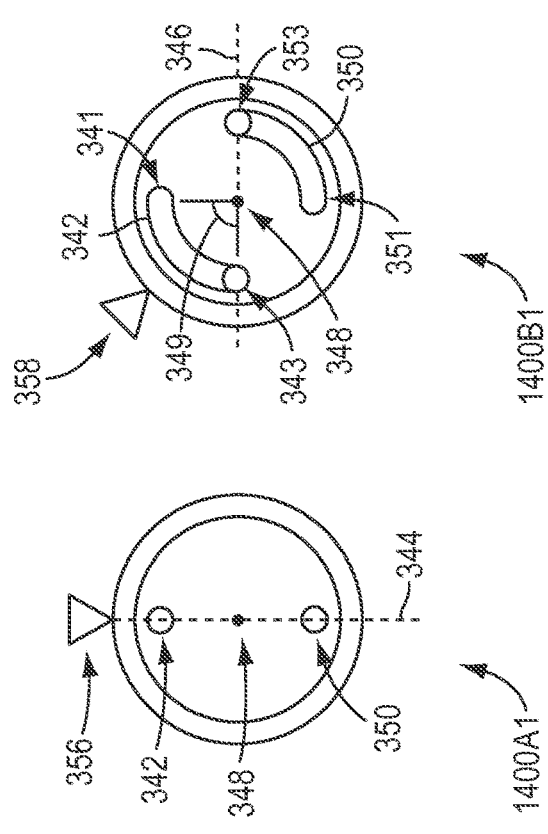
FIG. 14A  FIG. 14B  FIG. 14C  FIG. 14D

MECHANICAL JOINTS, AND RELATED SYSTEMS AND METHODS

RELATED APPLICATIONS

This application is the U.S. national phase of international application no. PCT/US2015/016854 (filed Feb. 20, 2015), which designated the United States and claimed right of priority to U.S. provisional patent application No. 61/934,084 (filed Feb. 21, 2014), both of which are incorporated herein by reference.

TECHNICAL FIELD

The present disclosure relates to mechanical joint structures and instruments and methods that utilize actuation elements to articulate mechanical joints. In particular, aspects of the present disclosure relate to surgical instruments and methods that utilize remotely actuatable mechanical joints.

BACKGROUND

Remotely controlled surgical instruments, including teleoperated surgical instruments, are often used in minimally invasive medical procedures. During medical procedures, surgical instruments may be articulated in one or more directions. For instance, the surgical instrument may be actuated by a transmission mechanism at a proximal end of the surgical instrument shaft to orient and position an end effector located at a distal end of the surgical instrument in a desired location. The surgical instrument may further include a wrist, such as a jointed, articulatable structure, that the end effector is connected to so that the end effector may be positioned relative to the shaft. The surgical instrument may further include one or more end effector actuation elements that pass through the surgical instrument, including the wrist, to actuate the end effector. Articulating (bending) the wrist may result in bending of the end effector actuation element(s), which may cause a change in the length of the end effector actuation element(s). Such a change in length can result in unintended motions of the end effector. In view of this, it may be desirable to provide a surgical instrument that includes one or more end effector actuation elements configured to substantially conserve the length of the actuation elements when a wrist of the instrument is articulated.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument may comprise a shaft comprising a wrist at a first end, an end effector coupled to the wrist, and an actuation element that extends along the shaft and the wrist. The actuation element may follow a twisted path along at least a portion of the wrist. The twisted path may have an angular extent of less than 360 degrees along an entire length of the wrist.

In accordance with another exemplary embodiment, a support structure for an actuation element of a surgical instrument may comprise at least one passage defining a twisted path about a longitudinal axis of the support structure. The passage may have an angular extent of less than 360 degrees from a first end of the passage to a second end of the passage.

In accordance with another exemplary embodiment, a method of configuring a surgical instrument wrist may comprise extending an actuation element along the wrist so the actuation element follows a twisted path along at least a portion of the wrist. The twisted path may have an angular extent of less than 360 degrees.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 14A shows a schematic cross-sectional view of a wrist of a surgical instrument, according to an exemplary embodiment.

FIG. 14B shows a schematic cross-sectional view of a wrist of a surgical instrument, according to an exemplary embodiment.

FIG. 14C shows a schematic cross-sectional view of a wrist of a surgical instrument, according to an exemplary embodiment.

FIG. 14D shows a schematic cross-sectional view of a wrist of a surgical instrument, according to an exemplary embodiment.

DETAILED DESCRIPTION

Figure 1:
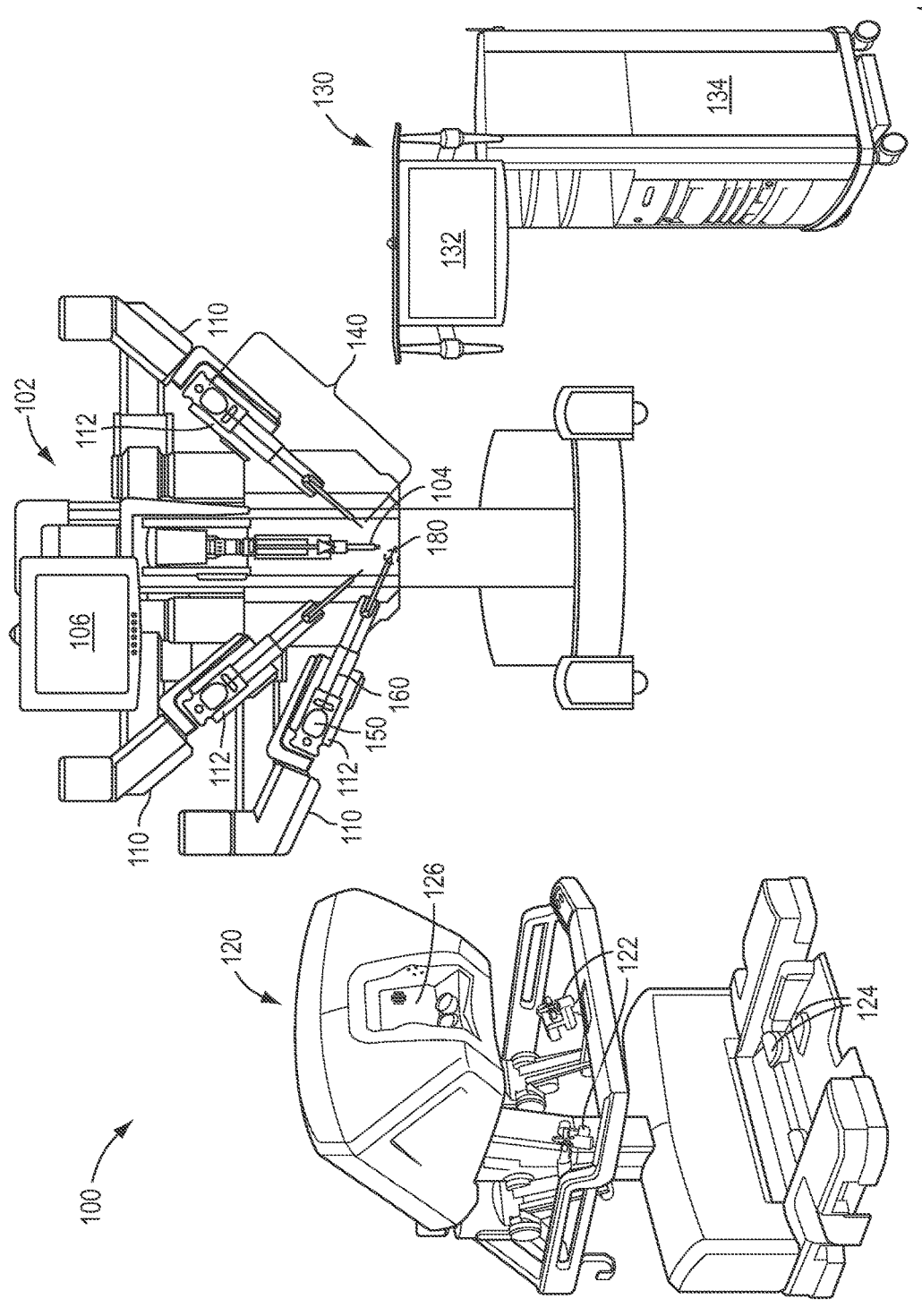
FIG. 1 shows a teleoperated surgical system, according to an exemplary embodiment.

This description and the accompanying drawings that illustrate exemplary embodiments should not be taken as limiting. Various mechanical, compositional, structural, electrical, and operational changes may be made without departing from the scope of this description and claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates surgical instruments for teleoperated surgical systems that utilize an actuation element, with at least a portion of the actuation element being arranged along a twisted path. The actuation element may be used to actuate an end effector, to articulate a wrist, or to actuate another component of an instrument. Further, the exemplary embodiments may be applied to any actuation element offset from a central longitudinal axis (neutral axis) of a surgical instrument. According to an exemplary embodiment, the twisted path may have an angular extent less than 360 degrees, relative to a centerline of the wrist, along an entire length of the wrist. According to an exemplary embodiment, at least a portion of an actuation element may be arranged along a twisted path so that the length of the actuation element is conserved at each joint of the wrist as the wrist actuates or bends. By conserving the length of the actuation element, changes in length of an actuation element, which might interfere with the actuation functions of the actuation element, that may otherwise occur during bending of a wrist may be minimized or eliminated. According to an exemplary embodiment, an actuation element may be arranged along a twisted path so that the length of the actuation element is conserved at an individual joint of a wrist but not conserved at another individual joint of the wrist, with the total twisted path of the actuation element being a length conservative structure.

The present disclosure further contemplates an actuation element support. An actuation element support may be used to shape at least a portion of an actuation element into a desired shape, such as along a twisted path, to conserve length of the actuation element and/or to increase the buckling strength of the actuation element. According to an exemplary embodiment, an actuation element support may be a single piece member that includes at least one lumen, wherein at least a portion of the lumen has a twisted shape. According to an exemplary embodiment, an actuation element support may include at least one rigid portion. An actuation element support may include, for example, a plurality of coaxial tubes, according to an exemplary embodiment. According to an exemplary embodiment, an actuation element support may comprise a tube with one or more areas of material weakness, such as cut-out grooves, to provide flexibility to the support. An actuation element support may include a hollow structure, such as a flexible shaft, useful for both pushing and pulling motions, according to an exemplary embodiment. A flexible shaft may be, for example, a wound spring connected to filaments. According to another exemplary embodiment, a flexible shaft may include multiple layers of wound filaments connected together.

Turning to FIG. 1, an example of a teleoperated surgical system 100 is shown that can employ surgical instruments in accordance with embodiments described herein. System 100, which may, for example, be a da Vinci® Surgical System available from Intuitive Surgical, Inc., includes a patient side cart 102 having multiple surgical instruments 140, each of which is mounted in a docking port on an arm 110. Instruments 140 can be interchangeable, so that the instruments 140 mounted on arms 110 can be selected for a particular medical procedure or changed during a medical procedure to provide the clinical functions needed. As is well known in the art, surgical instruments 140 can implement many functions including, but not limited to, for example, forceps or graspers, needle drivers, scalpels, scissors, cauterizing tools, and staplers.

Figure 8:
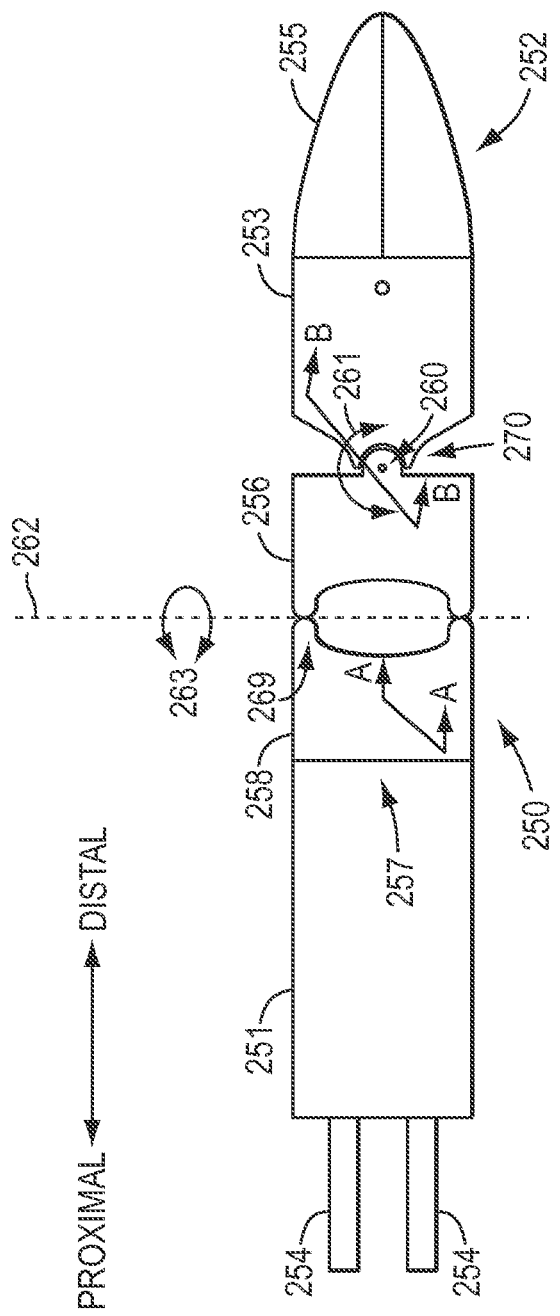
FIG. 8 is a side view of a distal portion of a surgical instrument, according to an exemplary embodiment.

Each instrument 140 generally includes a transmission or backend mechanism 150, a main shaft 160 extending from the transmission mechanism 150, an optional wrist (not shown in FIG. 1) at the distal end of main shaft 160, and an end effector 180 extending from wrist or directly from the shaft 160. For instance, FIG. 8 illustrates one exemplary embodiment of a distal end of a surgical instrument that includes, among other things, a shaft 251, a wrist 250 at a distal end of shaft 251, and an end effector 252 extending from wrist 250. Actuation elements 254, such as, for example, tendons or rods, may extend through shaft 251 to wrist 250 and/or to end effector 252. As those of ordinary skill in the art are familiar with, actuation elements may be configured as pull/pull or push/pull actuation elements. Exemplary embodiments of pull/pull and push/pull actuation devices are described in U.S. Pat. No. 8,545,515, issued Oct. 1, 2013, which is hereby incorporated by reference in its entirety. Thus, actuation elements 254 may be used to actuate wrist 250 and/or end effector 252. Thus, with reference to FIG. 1, actuation elements may extend from a transmission mechanism 150, which may be connected to a patient side manipulator 112. Transmission mechanism 150 typically provides a mechanical coupling of the actuation elements to drive motors in patient side cart 102. For instance, transmission mechanisms 150 may be configured to connect to patient side manipulators 112 of arms 110 of the patient side cart 102. As a result, patient side manipulators 112 and transmission mechanisms 150 may be used to apply a force to actuation elements 254 to actuate wrist 250 and/or end effector 252. Further, with reference again to FIG. 8, electrical conductors (not shown in FIG. 8) may also extend through shaft 251 and wrist 250 to end effector 252.

System 100 can thus control movement and forces along the actuation elements as needed to move or position a wrist and operate end effector 180. An arm 110 of patient side cart 102 can be used to insert the end of a surgical instrument 140 through a cannula in small incisions in a patient undergoing a medical procedure and to operate a wrist of instrument 140 and/or end effector 180 at a worksite inside the patient.

A camera instrument 104 can similarly be mounted on an arm of cart 102 and optionally also have a wrist that system 100 operates to position a distal end of camera system 104 for viewing of a work site and the operation of surgical instruments 140 within a patient. The views from camera system 104, which may be stereoscopic or three-dimensional, can be viewed at a control console (not shown) and images may be displayed on a monitor 106. A processing system of system 100 can thus provide a user interface enabling a doctor or other medical personnel to see and manipulate the camera system 104 and instruments 140. For example, as with surgical instruments 140, an arm 110 can be used to insert the end of a camera instrument 104 through a cannula in small incisions in a patient undergoing a medical procedure and to operate wrist and/or end effector 180 at a worksite inside the patient.

The diameter or diameters of main shaft 160, wrist, and end effector 180 for surgical instrument 140 and the diameter of camera instrument 104 are generally selected according to the size of the cannula with which the instrument will be used. In an exemplary embodiment, a diameter of camera instrument 104 and a diameter of wrist and main shaft 160 may range from about 3 mm to about 13 mm. For example, the diameter may be about 4 mm, about 5 mm, about 8 mm, about 10 mm, or about 13 mm to match the sizes of some existing cannula systems.

As illustrated in the schematic view of FIG. 1, the teleoperated surgical system 100 may further include a surgeon console 120 and an auxiliary control/vision cart 130. In general, the surgeon console 120 receives inputs from a user, e.g., a surgeon, by various input devices, including but not limited to, gripping mechanisms 122 and foot pedals 124, and serves as a master controller to which the instruments 140 mounted at the patient side cart 102 are responsive to implement the desired motions of the surgical instrument(s) 102, and accordingly perform the desired surgical procedure. For example, while not being limited thereto, the gripping mechanisms 122 may act as "master" devices that may control the surgical instruments 140 and/or camera instrument 104, which may act as the corresponding "slave" devices at the arms 110. For instance, gripping mechanisms 122 may control an end effector 180 and/or wrist of the surgical instrument 140, as those having ordinary skill in the art are familiar with. Further, while not being limited thereto, the foot pedals 124 may be depressed to provide, for example, monopolar or bipolar electrosurgical energy, or to activate a variety of other functions (e.g., suction, irrigation, and/or various other flux delivery modes) of the instruments 140. In other words, based on the commands provided to input devices at, for example, the surgeon console 120, the patient side cart 102 can position and actuate the instruments 140, 104 to perform a desired medical procedure via the patient side manipulators 112 at the arms 110. Thus, the instruments 140, 104 of patient side cart 102 may be remotely teleoperated according to commands inputed by a user at the surgeon console 120. Surgeon console 120 may further include a display to allow a surgeon to view a three-dimensional image of the surgical site, for example, during the surgical procedure, e.g., via the camera instrument 104 at the patient side cart 102.

In non-limiting exemplary embodiments of the teleoperated surgical system, the control/vision cart 130 includes "core" processing equipment, such as core processor 134, and/or other auxiliary processing equipment, which may be incorporated into or physically supported at the control/vision cart 130. The control/vision cart 130 may also include other controls for operating the surgical system. In an exemplary embodiment, signal(s) or input(s) transmitted from surgeon console 120 may be transmitted to one or more processors at control/vision cart 130, which may interpret the input(s) and generate command(s) or output(s) to be transmitted to the patient side cart 102 to cause manipulation of one or more of surgical instruments 140, 104 and/or arms 110 to which the surgical instruments 140, 104 are coupled at the patient side cart 102. It is noted that the system components in FIG. 1 are not shown in any particular positioning and can be arranged as desired, with the patient side cart 102 being disposed relative to the patient so as to affect surgery on the patient.

A surgical instrument may have one or more degrees of freedom, permitting the instrument to bend in one or more directions. For instance, the wrist may provide articulation to permit bending in one or more directions, such as in arbitrary pitch and yaw directions that are substantially orthogonal to one another. An instrument may include other joints that permit bending, such as a joggle joint described in U.S. Pat. No. 7,942,868, published May 17, 2011, and U.S. App. Pub. No. US 2008/0065105, published on Mar. 13, 2008, both of which are incorporated by reference herein in their entirety. Elements that pass through bent portions of an instrument, including actuation elements (e.g., tendons or rods) and electrical cables, such as for actuating a wrist or an end effector, are also bent.

Figure 2:
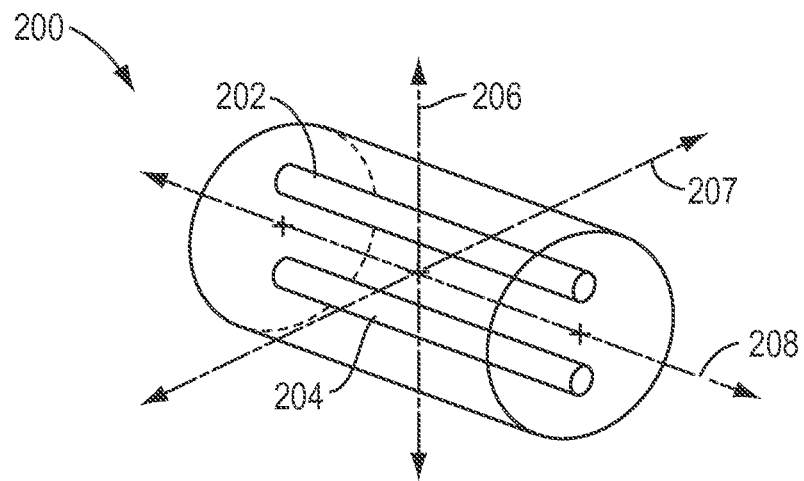
FIG. 2 shows a schematic perspective view of a single flexible and bendable member in a straight configuration, according to an exemplary embodiment.
Figure 3:
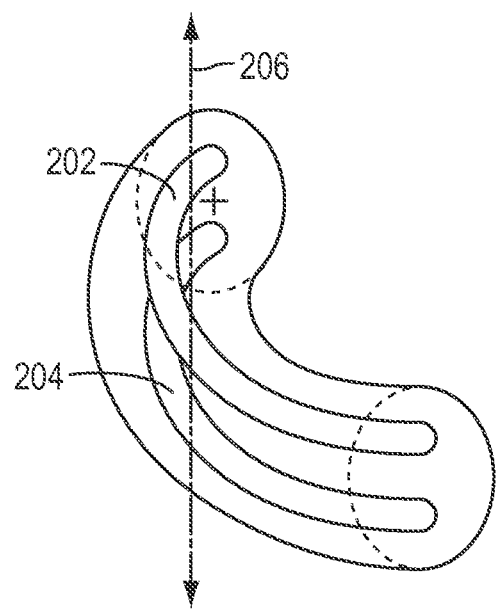
FIG. 3 shows the member of FIG. 2 in a bent configuration.

Bending may have an effect upon actuation elements when the actuation elements pass through bent portions of a surgical instrument. Turning to FIG. 2, a schematic perspective view is shown of a single flexible member 200 that can bend like a joint. A first actuation element 202 and a second actuation element 204 extending through member 200, such as along a longitudinal axis 208 of member 200. In the exemplary embodiment of FIG. 2, wherein member 200 is in a straight (neutral) configuration, a bending axis 206 passes through each of first actuation element 202 and second actuation element 204. As shown in FIG. 3, when member 200 is bent around bending axis 206, first and second actuation elements 202, 204 bend as well. Because axis 206 passes through both of actuation elements 202, 204, there is no relative change in length between first actuation element 202 and second actuation element 204. In other words, one of actuation elements 202, 204 does not become substantially longer or substantially shorter than the other.

Figure 4:
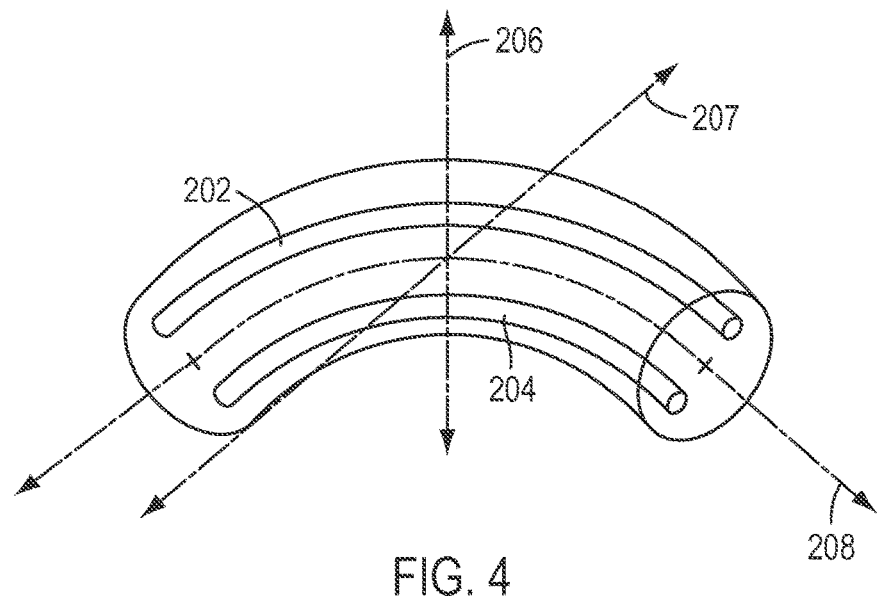
FIG. 4 shows the member of FIG. 2 in a bent configuration.

Turning again to FIG. 2, a second bending axis 207 for member 200 passes between first actuation element 202 and second actuation element 204. As a result, when member 200 is bent in the manner shown in FIG. 4 about bending axis 207, first actuation element 202 is stretched relative to its neutral position, causing a positive change in its length, while second actuation element 204 is compressed relative to its neutral position, causing a negative change in its length. Therefore, bending member 200 relative to bending axis 207 can cause a change in the relative lengths of actuation elements 202, 204, with one actuation element becoming longer the other. Such a relative change in length can interfere with the function of actuation elements, such as to actuate an end effector. For instance, when actuation elements 202, 204 are used to open and close an end effector by applying tension or compression to actuation elements 202, 204, a relative change in length between actuation elements 202, 204 may create slack in one of the actuation elements 202, 204, diminishing the ability of the actuation element to transmit the desired tension or compression and cause a desired actuation of an end effector.

In view of these considerations, it may be desirable to design a joint of a surgical instrument so that a bend axis of the joint extends through an actuation element. For instance, a single actuation element may be provided to actuate an end effector, with the single actuation element extending along a center of a surgical instrument. In such a configuration, bending axes that are substantially orthogonal to one another, such as to provide two degrees of freedom for bending a surgical instrument, may pass through the center of the instrument and the actuation element. As a result, the length of the actuation element does not substantially change when the surgical instrument is bent around either bending axis. However, although this approach can be useful when a single actuation element is sufficient to control an end effector, a surgical instrument may include multiple actuation elements, such as to actuate different components of the instrument or to actuate an end effector or wrist that requires more than one actuation element.

Figure 5:
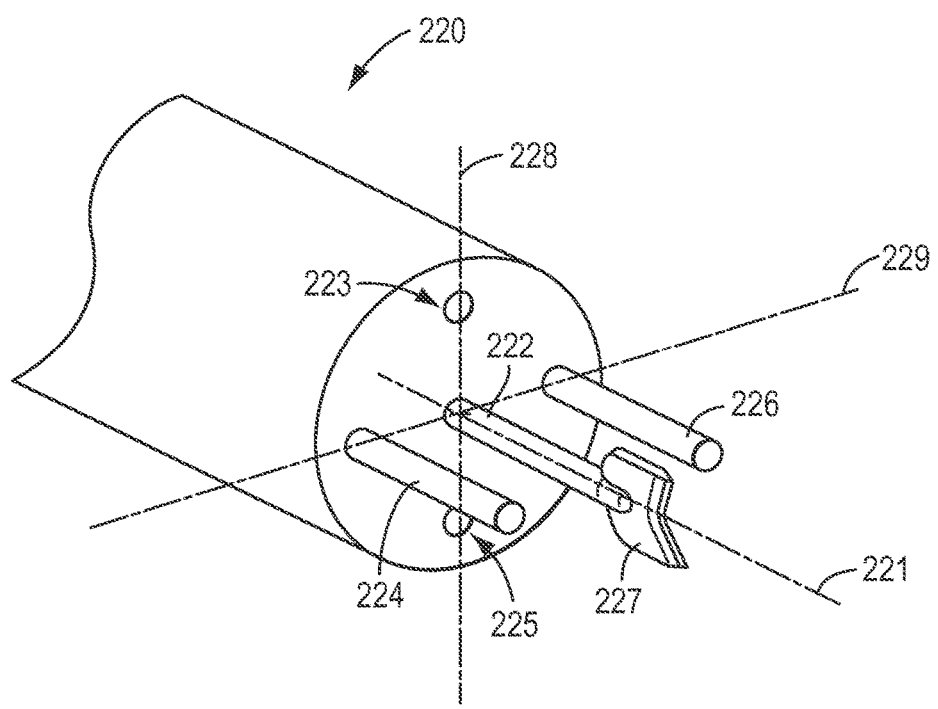
FIG. 5 is a partial schematic perspective cross-sectional view of an exemplary embodiment of a surgical instrument shaft and components extending through the shaft.

FIG. 5 illustrates an example of a surgical instrument 220 that includes multiple actuation elements. In various exemplary embodiments, surgical instrument 220 may be a surgical instrument configured according to the exemplary embodiments described in U.S. App. Pub. No. US 2012/0215220, published on Aug. 23, 2012; U.S. App. Pub. No. US 2012/0310254, published on Dec. 6, 2012; and U.S. App. Pub. No. US 2012/0310221, published on Dec. 6, 2012, which are each hereby incorporated by reference in their entirety. As illustrated, surgical instrument 220 includes a first component actuation element 222 that extends along a centerline 221 of surgical instrument 220. First actuation element 222 may be configured, for example, to actuate a cutting blade 227 or other component by pushing or pulling cutting blade along centerline 221.

Because first actuation element 222 is located along centerline 221, both pitch and yaw bend axes 228, 229 of instrument 220 pass through first actuation element 222. As a result, first actuation element 222 does not substantially experience a change in length when surgical instrument 220 is bent relative to axis 228 or axis 229. Surgical instrument 220 also includes other actuation elements, such as second and third end effector actuation elements 224, 226 to actuate, for example, an end effector (not shown) of instrument 220.

The end effector may be, for example, forceps or graspers, needle drivers, scalpels, scissors, cauterizing tools, staplers, or other types of end effectors, for example, jawed end effectors, used in the art. According to an exemplary embodiment, actuation elements 224, 226 may be pull/pull actuation elements that open and close an end effector by paying out one of actuation elements 224, 226 and pulling the other of actuation elements 224, 226, as one of ordinary skill in the art is familiar with. Surgical instrument 220 may include additional lumens 223, 225 for other components, such as, for example, additional actuation elements or flux conduits, such as conductors providing electrosurgical energy or other flux supplies to an end effector.

Because first actuation element 222 is present, actuation elements 224, 226 cannot be located along centerline 221 and axis 228 does not pass through actuation elements 224, 226. Thus, when surgical instrument 220 is bent relative to axis 228, a change in length may occur between actuation elements 224, 226. Due to these changes in length of actuation elements 224, 226 during bending, greater mechanical complexity is required for instrument 220 to decouple actuation elements 224, 226 from each other for actuation of an end effector.

In view of these considerations, the present disclosure contemplates surgical instruments having one or more actuation elements that do not substantially exhibit an overall change in length during bending, even when the actuation element position is offset from a bending axis. When an actuation element's overall change in length during bending is minimal, the mechanical complexity of an instrument including the actuation element may be reduced. In addition, by making an actuation element that does not substantially change its overall length due to bending (in other words, conserving the length of the actuation element), the actuation element may be decoupled from motion of a joint that the actuation element extends through. In other words, despite articulation of such joint(s), bending of the actuation element will not result in undesired or unintended actuation of an end effector.

One way to minimize or prevent an overall change in the length of an actuation element due to bending is to arrange the actuation element along a twisted path as it passes through a bending portion of a surgical instrument. For instance, an actuation element may be arranged along a twisted path having an angular extent of 360° for each bending axis the actuation element passes through to substantially minimize or prevent a change in the overall length of the actuation element (i.e., conserve the length of the actuation element).

Figure 6:
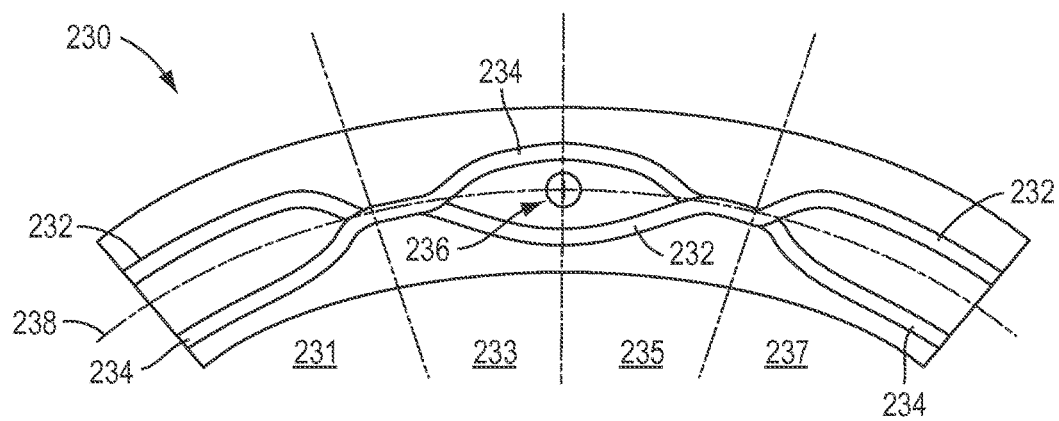
FIG. 6 is a top schematic view of an exemplary embodiment of a wrist of a surgical instrument.

Turning to FIG. 6, a schematic view of an exemplary embodiment of a wrist 230 of a surgical instrument is shown that includes a first actuation element 232 and a second actuation element 234. Wrist 230 may include a joint (not shown in the schematic view of FIG. 6) to cause bending of wrist 230 about a bend axis 236 (which extends into and out of the page of FIG. 6). Wrist 230 is bent about the bend axis 236, causing portions of actuation elements 232, 234 above longitudinal axis 238 in FIG. 6 to experience a positive change in length and portions below axis 238 to experience a negative change in length. Because actuation elements 232, 234 are arranged along a twisted path having an angular extent of 360° about axis 238 through wrist 230, actuation elements 232, 234 do not substantially experience a change in length due to bending wrist 230 about axis 238. For instance, although the portion of actuation element 232 in zone 231 experiences a positive change in length, the portion of actuation element 232 in zone 233 experiences a negative change in length that effectively cancels out the positive change in length from zone 231. Similarly the negative change in length of actuation element 232 in zone 235 is canceled out by the positive change in length of actuation element 232 in zone 237. Similar cancellations of changes in length between zones 231, 233, 235, 237 occur for actuation element 234 but in the opposite manner because actuation element 234 is positioned opposite to actuation element 232 about axis 238.

Figure 7:
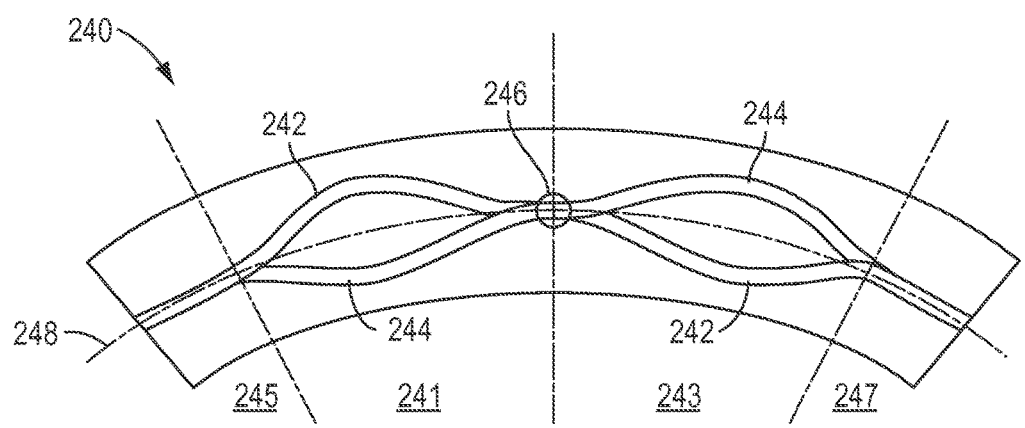
FIG. 7 is a top schematic view of an exemplary embodiment of a wrist of a surgical instrument.

Turning to FIG. 7, a schematic view of another exemplary embodiment of a wrist 240 is shown that includes a first actuation element 242 and a second actuation element 244, with wrist 240 bent about a bend axis 246. Similar to the exemplary embodiment of FIG. 6, wrist 240 may include joint (not shown in the exemplary embodiment of FIG. 7) to cause bending of wrist 240 about bend axis 246. In the exemplary embodiment of FIG. 7, at ends of zones 245, 247 of wrist 240, actuation elements 242, 244 are positioned along neutral axis 248, instead of being offset from neutral axis, as in the exemplary embodiment of FIG. 6. However, the actuation elements 242, 244 are arranged along a twisted path and offset from the longitudinal axis 248 in zones 241 and 243. Because actuation elements 242, 244 are arranged along a twisted path having an angular extent of 360° as they pass through wrist 240, the overall lengths of actuation elements 242, 244 do not substantially change. For instance, although the portion of actuation element 242 in zone 241 experiences a positive change in length, the portion of actuation element 242 in zone 243 experiences a negative change in length that cancels the positive change in length. Actuation element 244 experiences a similar cancellation of changes in length but in the opposite manner. The portions of actuation elements 242, 244 in zones 245, 247 do not experience any significant change in length relative to each other along the longitudinal axis 248.

As discussed above with regard to the exemplary embodiments of FIGS. 6 and 7, actuation elements offset from a central longitudinal axis (neutral axis) of a surgical instrument may be arranged along a twisted path having an angular extent of 360° for a bend axis of the surgical instrument. However, a surgical instrument may include several bend axes. For instance, a wrist of a surgical instrument may include one or more multi-DOF (degree of freedom) joints and thus plural bend axes. For instance, if wrist 230 of the exemplary embodiment of FIG. 6 includes a plurality of bend axes 236 extending in substantially the same direction, actuation elements 232, 234 may be arranged along a twisted path having an angular extent of 360° across both bend axes instead of just one bend axis.

According to another exemplary embodiment, a wrist including a first plurality of bend axes extending in one direction, such as in the direction of bend axis 236 in FIG. 6, and a second plurality of bend axes extending in another direction, such as substantially perpendicular to bend axis 236 in FIG. 6, actuation elements may be arranged along a twisted path having an angular extent of 360° across the first plurality of bend axes and along a twisted path having an angular extent of 360° across the second plurality of bend axes. However, twisting actuation elements along a twisted path to result in minimal or no change of length for each bend axis (e.g., when the bend axes extend in different or alternating directions) may result in increased friction between a twisted actuation element and surfaces that support and/or guide the actuation element into a twisted shape. Friction between an actuation element and its supporting surfaces may be represented by the capstan equation, $T_{load}=T_{hold}e^{\mu\phi}$, in which $T_{hold}$ is tension applied to the actuation element, μ is the coefficient of friction between the actuation element and support surface, φ is the total angle swept by the twist of the actuation element, and Toad is the force between the actuation element and supporting surface. Twisting an actuation element through a large angle of φ thus results in a large $T_{load}$ force between the actuation element and the support surface(s). Thus, twisting an actuation element 360 degrees for each joint, when the joints have bend axes extending in different or alternating directions, may pose difficulties in manufacturing, particularly for a relatively short length and small diameter of a wrist of a surgical instrument. In view of these considerations, the present disclosure contemplates surgical instruments including one or more joints that conserve the length of one or more actuation elements when bent (i.e., the overall length of the actuation elements does not significantly change when bent) while also minimizing the amount of twist to accomplish length conservation.

Various exemplary embodiments useful to provide length conservation of actuation elements are contemplated by the present disclosure and are discussed in further detail below with regard to jointed structures of a surgical instrument. Various jointed structures can use actuation element configurations that follow a twisted path. For example, the jointed structures may be for wrists, such as, for example, a wrist configured according to the exemplary embodiments of U.S. Provisional Application No. 61/943,068, entitled "Mechanical Wrist Joints with Enhanced Range of Motion, and Related Devices and Methods," filed on Feb. 21, 2014, and International PCT Application No. PCT/US15/16879, filed on a date even herewith and claiming priority to U.S. Provisional Application No. 61/943,068, each of which is hereby incorporated by reference in its entirety. In another example, the jointed structures may be used in joggle joints, such as, for example, the joggle joints described in U.S. Pat. No. 7,942,868, published May 17, 2011, and in U.S. App. Pub. No. US 2008/0065105, published Mar. 13, 2008.

Another type of joint with which exemplary embodiments of the present disclosure can be utilized is shown in the exemplary embodiment of FIG. 8. As noted above, FIG. 8 shows wrist 250 connected to an end effector 252. End effector 252 may include, for example, a clevis 253 and jawed member 255, according to an exemplary embodiment. According to an exemplary embodiment, wrist 250 includes a first link 256 connected to end effector 252 and a second link 258, with a joint 270 connecting first link 256 to end effector 252 and a joint 269 connecting second link 258 to first link 256. The links in various exemplary embodiments described herein can be configured as disks, as those having ordinary skill in the art are familiar with. However, other shapes can also be employed without departing from the scope of the disclosure and claims. In exemplary embodiments in which end effector 252 is directly jointed to first link 256 via joint 270, at least a portion of end effector 252 is a part of wrist 250.

According to another exemplary embodiment, a wrist may include three links instead of two links. For instance, instead of having link 256 directly connected to a clevis 253 to provide a joint 270 between link 256 and clevis 253, as shown in the exemplary embodiment of FIG. 8, a third link may be provided between link 256 and clevis 253, with joint 270 formed between link 256 and the third link and the link attached to clevis.

First link 256 and clevis 253 may be articulated relative to one another about axis 260 (which extends into and out of the page of FIG. 8) in direction 261. Wrist 250 further includes a second link 258 connected to first link 256 so that second link 258 and first link 256 may be articulated relative to one another about axis 262 in direction 263. Axes 260, 262 may be substantially orthogonal to one another to provide wrist 250 with two degrees of freedom, such as motion in arbitrarily selected pitch and yaw directions. Because wrist 250 has two degrees of freedom with motion in different directions, wrist 250 may be described as an "AB" wrist, which refers to the two different motions provided by the joints 269, 270 of wrist 250.

Figure 9:
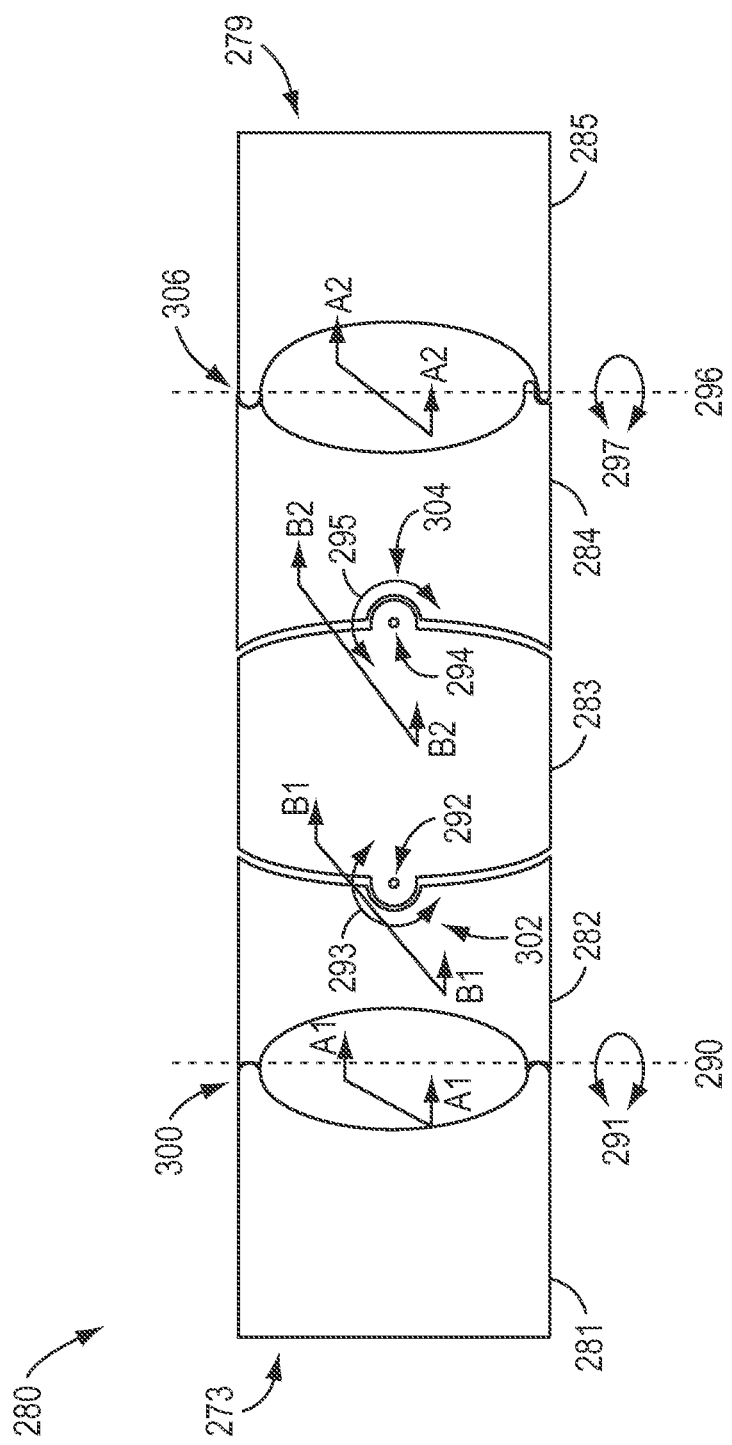
FIG. 9 is a side view of an exemplary embodiment of a wrist of a surgical instrument.

The exemplary embodiments described herein may be used in wrists other than "AB" type wrists. For example, wrists may include a plurality of joints of the same bend axis type, which can provide a larger range of motion of a wrist. Turning to FIG. 9, an exemplary embodiment of a wrist 280 is shown that includes links 281-285. Links 281 and 282 are connected so that they may articulate relative to one another about axis 290 in direction 291. Links 284 and 285 are connected to one another in substantially the same way as links 281 and 282, with links 284 and 285 articulating relative to one another about axis 296 in direction 297. Thus, the joint 300 between links 281 and 282 and the joint 306 between links 284 and 285 are the same type and may be referred to as "A" joints. Links 282 and 283 are connected so that they may articulate relative to one another about axis 292 (which extends into and out of the page of FIG. 9) in direction 293. Axes 290, 292 may be substantially orthogonal to one another to provide wrist 280 with two degrees of freedom, such as motion in arbitrary pitch and yaw (or A and B) directions. Further, links 283 and 284 are connected to one another in substantially the same way as links 282 and 283, with links 283 and 284 articulating relative to one another about axis 294 (which extends into and out of the page of FIG. 9) in direction 295. The joint 302 between links 282 and 283 and the joint 304 between links 283 and 284 are the same type and may be referred to as "B" joints. Thus, wrist 280 may be referred to as an "ABBA" wrist, which refers to the order of the bend axis types of the joints along wrist 280.

In another example, a wrist may have an "ABAB" configuration. Such a configuration, for instance, may include two "AB" joints, such as the links 256, 258 of the exemplary embodiment of FIG. 8 in series so that two "AB" joints are directly connected to one another in an "ABAB" configuration.

Due to the small size of a wrist for a surgical instrument and the various complicated components of a wrist, which may have different movements in different directions, various issues arise in passing actuation elements through a wrist, including determining how to pass actuation elements through a wrist to minimize how much the actuation element extends in a twisted shape through the wrist while substantially conserving the length of the actuation element as the wrist is bent. Various exemplary embodiments herein contemplate a wrist of a surgical instrument in which one or more actuation elements extend along a twisted path having an angular extent of less than 360° along the entire length of the wrist. These designs account for, among other things, for example, the angular extent traversed by an actuation element along a twisted path across an entire length of a wrist, the angular extent traversed by an actuation element along a twisted path across individual bending axes, the angular extent traversed by an actuation element and the resulting friction between the actuation element and support surface(s) (i.e., minimizing the angular extent minimizes the amount of friction to overcome, such as per the capstan equation, when applying a force to actuate the actuation element), and the initial angle of an actuation element relative to a bending axis.

Figure 10A:
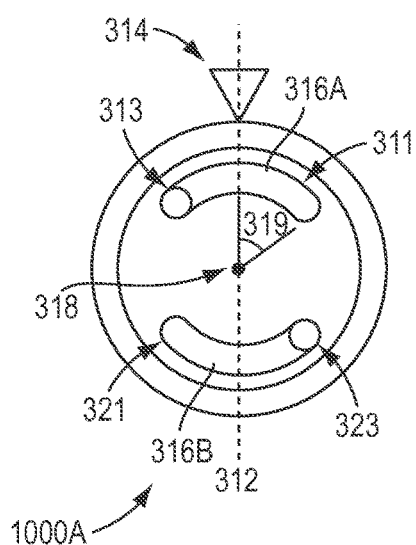
FIG. 10A shows a schematic cross-sectional view of a wrist, according to an exemplary embodiment.
Figure 10B:
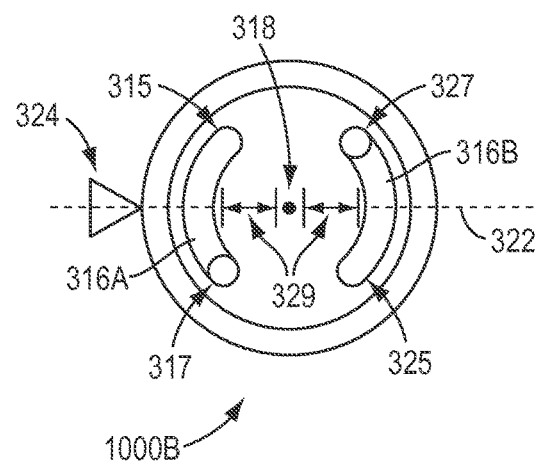
FIG. 10B shows a schematic cross-sectional view of a wrist, according to an exemplary embodiment.

Turning to FIGS. 10A and 10B, cross-sectional schematic views are shown of two joints 1000A and 1000B of a wrist. The wrist can be structured similarly to the wrist 250 of the exemplary embodiment of FIG. 8, according to an exemplary embodiment. For instance, the cross-sections of joints 1000A and 1000B in FIGS. 10A and 10B may be schematic views along lines A-A and B-B of the exemplary embodiment of an AB wrist in FIG. 8, but modified to show the amount of twist of actuation elements 316A, 316B as they extend across each joint 1000A and 1000B. Actuation elements 316A, 316B may be used, for example, to actuate an end effector (such as end effector 252 of the exemplary embodiment of FIG. 8) or to actuate another component of an instrument, such as, for example, a wrist. According to an exemplary embodiment, actuation elements 316A, 316B may follow a twisted path so that actuation of actuation elements 316A, 316B does not result in an inverted motion, such as when actuation elements 316A, 316B are used to actuate a wrist.

The cross-sections in FIGS. 10A and 10B respectively represent two different joints 1000A and 1000B of a wrist with the cross-section for joint 1000A representing a joint (such as joint 269 in the exemplary embodiment of FIG. 8) having a bending axis 312 and cross-section for joint 1000B representing a joint (such as joint 270 in the exemplary embodiment of FIG. 8) having a bending axis 322.

The actuation elements of the various exemplary embodiments described herein may be substantially length conservative. Thus, although in some cases an actuation element may have zero change in length when joint(s) through which the actuation element extends are actuated, such as one or more joints of a wrist, in some cases the actuation element may experience a small amount of change in length. According to an exemplary embodiment, a substantially length conservative actuation element may experience a change in length of, for example, less than about 0.010 inches, including no change in length, such as when 10 pounds or less of tension is applied to the actuation element.

The angular extent of twist of actuation elements 316A, 316B may be selected to make actuation elements 316A, 316B length conservative over the wrist. For instance, each of actuation elements 316A, 316B may have a twist of 90° for each joint 1000A, 1000B of the wrist, as shown in FIGS. 10A and 10B. In other words, actuation elements 316A, 316B may have an angular extent of 90° with respect to centerline 318 for each joint 1000A, 1000 B. For example, actuation element 316A may be arranged along a twisted path having an angular extent of about 90° from an initial position 311 to a subsequent position 313 across joint 1000A. Further, actuation element 316A may be twisted 90° from an initial position 315 (corresponding to subsequent position 313 in the cross-section for joint 1000A) to a subsequent position 317 across joint 1000B.

Figure 11:
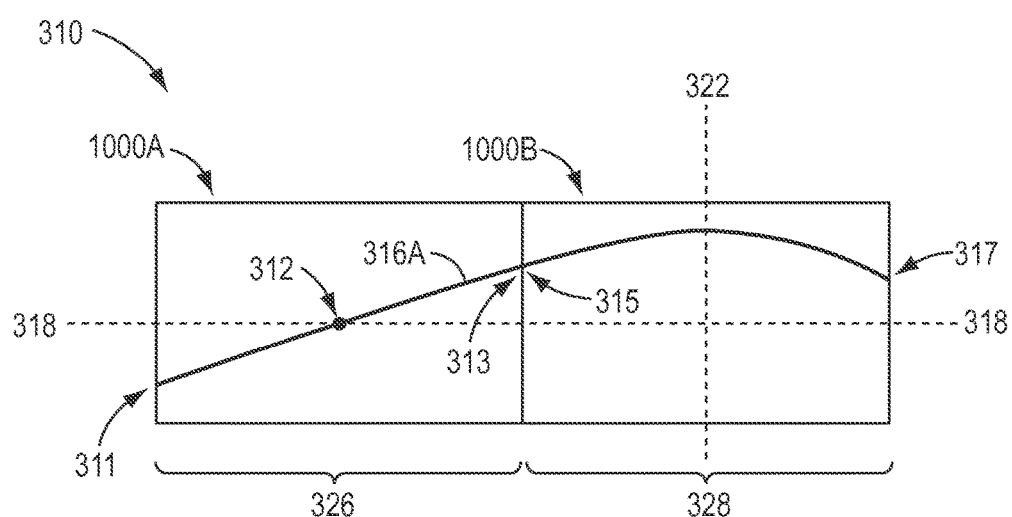
FIG. 11 shows a top view schematically illustrating the shape of an actuation element along a wrist.

To facilitate viewing of the twist of an actuation element, FIG. 11 shows a schematic top view of a wrist 310 including the joints depicted in FIGS. 10 A and 10B, with only actuation element 316A shown along the length of the joints 1000A, 1000B of wrist 310 to illustrate the shape of actuation element 316A along different joints of wrist 310. In FIG. 11, wrist 310 has been schematically segmented into joint 1000A and joint 1000B to show the amount of twist of actuation element 316A along each of joints 1000A and 1000B. According to an exemplary embodiment, joint 1000A may have a length 326 and joint 1000B may have a length 328, which are schematically shown in the exemplary embodiment of FIG. 8 for purposes of depicting the amount of twist for joints 1000A and 1000B. With reference to the exemplary embodiment of FIG. 8, joint 1000A may correspond to, for example, joint 269, with the twist for joint 1000A being substantially centered at joint 269 and extending for substantially equal amounts on either side of joint 269.

Similarly, with reference to the exemplary embodiment of FIG. 8, joint 1000B may correspond to, for example, joint 260, with the twist for joint 1000B being substantially centered at joint 270 and extending for substantially equal amounts on either side of joint 270. As shown in FIG. 11, actuation element 316A may be twisted from an initial position 311 to a subsequent position 313 over joint 1000A and twisted from an initial position 315 to a subsequent position 317 over joint 1000B. According to an exemplary embodiment, the twist of an actuation element may be substantially continuous, as shown in FIG. 11, as actuation element 316A is twisted over joints 1000A and 1000B. Using a substantially continuous twist may beneficially minimize the amount of friction between an actuation element and support structure because the twist may occur over a longer longitudinal length of a wrist.

The twist of actuation elements, however, is not limited to the substantially continuous twists shown in the exemplary embodiment of FIG. 11. For instance, actuation elements may be twisted into sections having varying amounts of twist along the length of the actuation elements. In another instance, actuation elements may instead follow a discontinuous twisted path including twisted portions separated by one or more regions in which an actuation element extends straight and substantially parallel to the neutral axis of a wrist. In such discontinuous twist embodiments, the twist of actuation elements 316A, 316B may still be in the amounts shown in FIGS. 10A and 10B (i.e., 90°) but over a shorter span of the lengths 326, 328 of joints 1000A and 1000B in FIG. 11 due to the inclusion of one or more straight, non-twisted portions of actuation elements 316A, 316B.

As best shown in FIGS. 10A and 10B, actuation element 316A is twisted 90° for each of joints 1000A and 1000B about a neutral axis 318 (i.e., has a twisted shape with an angular extent of 90° with respect to centerline 318 for each of joints 1000A and 1000B). According to an exemplary embodiment, neutral axis 318 may be a longitudinal centerline of wrist 310. In addition, axis 318 may be a longitudinal centerline of wrist 310 as well as a centerline for the twisted path that the actuation elements 316A, 316B follow, according to an exemplary embodiment. Actuation element 316A may be radially spaced a distance 329 from neutral axis 318, as shown in the cross-section of joint 1000B in FIG. 10B. Actuation element 316B is also spaced radial distance 329 from neutral axis, as shown in the cross-section of joint 1000B in FIG. 10B. Radial distance 329 may vary according to the diameter of wrist 310. Radial distance 329 may be, for example, greater than about 0 mm to about 10 mm when an actuation element does not extend along neutral axis 318 (e.g., is spaced a non-zero radial distance from neutral axis 318). According to another exemplary embodiment, radial distance 329 may be, for example, greater than about 0 mm to about 6 mm According to an exemplary embodiment, radial distance 329 may be maximized so that actuation elements 316A, 316B are spaced at or near the periphery of joints 1000A and 1000B, such as to maximize an internal space within wrist 310. According to another exemplary embodiment, radial distance 329 may be minimized so that actuation elements 316A, 316B are spaced near neutral axis 318, such as when actuation elements 316A, 316B and/or guide lumens for actuation elements 316A, 316B are difficult to bend.

Similarly to actuation element 316A, actuation element 316B may also be twisted 90° (i.e., have an angular extent of 90° along a twisted path about centerline 318) from an initial position 321 to a subsequent position 323 in the joint represented by cross-section 1000A, as shown in FIGS. 10A and 11. Further, actuation element 316B may be twisted 90° from an initial position 325 (coincident with subsequent position 323 in cross-section 1000B) to a subsequent position 327 in the joint represented by cross-section 1000B, as shown in FIGS. 10B and 11. Thus, each of actuation elements 316A, 316B may have a total of 180° of twist (i.e., have an angular extent of 180° along a twisted path about centerline 318) over the entire length of wrist 310 to make actuation elements 316A, 316B length conservative over wrist 310. This results in an overall twist of each actuation element 316A, 316B being substantially smaller than a 360° twist.

For instance, when considering the twist of actuation element 316A about centerline 318, such as when neutral axis 318 is an origin in a polar coordinate system, actuation element 316A is twisted through an angle measure of 180° across the entire length of wrist 310 from initial position 311 in joint 1000A to subsequent position 317 in joint 1000B. This is further illustrated in the exemplary embodiment of FIG. 33, which depicts a twisted path 900. As shown in the exemplary embodiment FIG. 33, twisted path 900 extends in a twisted shape around a longitudinal axis 908 (i.e., centerline 908) from a first end 902 to a second end 906. To show the angular extent of twisted path 900, twisted path 900 may be projected as an arc 910 having a radius of curvature 913 onto a plane 901, with points on arc 910 corresponding to locations on twisted path 900. For instance, point 912 on arc 910 may correspond to a first end 902 of twisted path 900 and point 914 on arc 910 may correspond to a point 904 approximately halfway along the length of twisted path 900.

Figure 21:
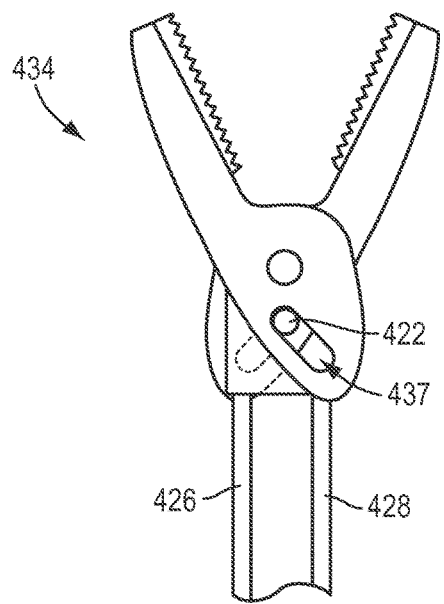
FIG. 21 shows the end effector of FIG. 20 in an open configuration.

Although twisted path 900 is depicted in the exemplary embodiment of FIG. 21 as having a substantially constant radius of curvature 913, twisted path 900 (and therefore arc 910) may include sections having differing curvatures and/or may also include one or more straight sections. Therefore, when a twisted path is discussed in the exemplary embodiments herein, the twisted path may twist with a substantially continuous radius of curvature or may include sections with differing radii of curvature, including curved sections with differing radii of curvature and/or straight sections.

Figure 33:
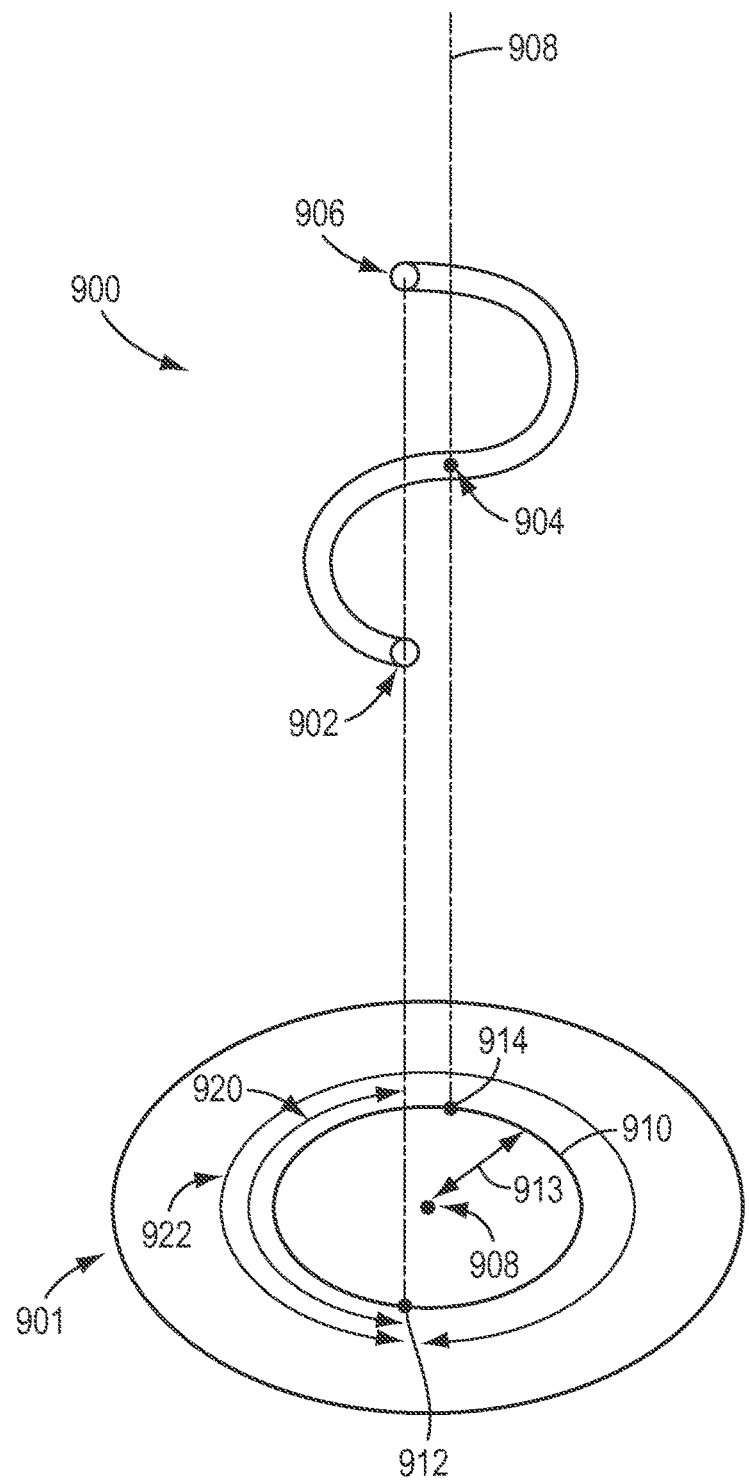
FIG. 33 is a perspective view of a twisted shape and projection of the angular extent of the twisted shape, according to an exemplary embodiment.

As shown in FIG. 33, an angular extent 920 between point 912 and point 914 on arc 910, relative to centerline 908 (which may also be projected onto plane 901), is approximately 180°. Thus, when the angular extent of a twisted path is discussed in the exemplary embodiments herein, the angular extent may be determined according to angular extent 920 relative to centerline 908, as shown in FIG. 33. Further, because twisted path 900 completes a full 360° twist from first end 902 to second end 906, point 912 on arc 910 corresponds to both first end 902 and second end 906, with the angular extent 922 between first end 902 and second end 906 being 360°. Thus, in the exemplary illustration of FIG. 33, arc 910 forms a complete circle. However, in other embodiments in which a twisted path does not complete a 360° twist, arc 910 will not complete a circle because the angular extent of the twisted path is less than 360°.

Twisting actuation elements 316A, 316B in the manner shown in FIGS. 10A, 10B, and 11 can permit actuation elements 316A, 316B to be length conservative for wrist 310. Further, according to an exemplary embodiment, the angular extent of twist of actuation elements 316A, 316B may be selected to make actuation elements 316A, 316B length conservative for each of joints 1000A and 1000B. For example, for joint 1000A, approximately half of each of the actuation elements 316A, 316B is on the left side of bend axis 312 and approximately half of each of the actuation elements 316A, 316B is on the right side of bend axis 312, as shown in the schematic depiction of the exemplary embodiment of FIG. 10A. As a result, any positive or negative change in length for the portion of actuation elements 316A, 316B on the left side of bend axis 312 is offset by any negative or positive change in length for the portion of actuation elements 316A, 316B on the right side of bend axis 312. Thus, there is substantially no net change in length for actuation elements 316A, 316B, making each of actuation elements 316A, 316B length conservative across joint 1000A. Similarly, for joint 1000B, approximately half of each actuation elements 316A, 316B is on the top side and on the bottom side of bend axis 322, as shown in the schematic depiction of the exemplary embodiment of FIG. 10B, so that any change in length for the top side of actuation elements 316A, 316B relative to bend axis 322 is substantially offset by any change in length for the bottom side of actuation elements 316A, 316B relative to bend axis 322. Thus, there is substantially no net change in length for actuation elements 316A, 316B, making actuation elements 316A, 316B length conservative across joint 1000B.

An amount of twist of an actuation member across a joint may also be schematically represented by the average angular position of the actuation member over a length of a joint. For instance, an average angular position 314 of actuation element 316A with regard to neutral axis over the length 326 of joint 1000A is schematically shown in FIG. 10A. In other words, as actuation elements 316A twists through 90° across the length 326 of joint 1000A, such as when neutral axis 318 is treated as an origin in a polar coordinate system, an average angular position 314 of actuation element 316A may be determined. When average angular position 314 of actuation element 316A across the length 326 of joint 1000A lines up with bend axis 312 for joint 1000A, as shown in FIG. 10A, this indicates that actuation element 316A is length conservative for joint 1000A. Actuation element 316A has an average angular position 324 across the length 328 of joint 1000B that also lines up with bend axis 322, as shown in FIG. 10B. Further, because actuation element 316B is positioned opposite to actuation element 316A and substantially mirrors the twist of actuation element 316A, the average angular positions of actuation element 316B across joints 1000A and 1000B may be considered to be the same as average angular positions 314, 324 of actuation element 316A.

As noted above, various exemplary embodiments account for an initial angle of an actuation element to a bending axis. An initial angle may be considered an initial angle of an actuation element to a bend axis as the actuation element enters a joint. As shown in the exemplary embodiment of FIG. 10A, actuation element 316A may have an initial angle 319 at its initial position 311 to bend axis 312 in joint 1000A. According to an exemplary embodiment, initial angle 319 may be approximately 45°, particularly when actuation element is twisted 90° along the length 326 of joint 1000A so that a substantially equal amount of actuation element may be located on either side of bend axis 312, as shown in the cross-sectional view of FIG. 10A. Because actuation element 316B may be positioned opposite to actuation element 316A across neutral axis 318, an initial position 323 of actuation element 316B in joint 1000A may be at approximately the same angle 319 with respect to bend axis 312, such as, for example, approximately 45°. In joint 1000B the initial positions 315, 325 of actuation elements 316A, 316B may be at an angle to bend axis 322 that is approximately the same as angle 319 in joint 1000A.

Other initial angles also may be utilized, however, such as when smaller or larger amounts of angular extent (twist) are used over a given joint. For example, an initial position 311 of actuation element 316A may be at an angle 319 of approximately 50° with respect to bend axis 312. In such an example, an amount of twist of actuation element 316A over joint 1000A may be approximately 100° so that a substantially equal amount of actuation element 316A may be positioned on either side of bend axis 312 and actuation element 316A is length conservative across joint 1000A. Other values for initial angle 319 are contemplated by the exemplary embodiments herein, such as, for example, about 40° to about 60°, according to an exemplary embodiment.

Figure 12A:
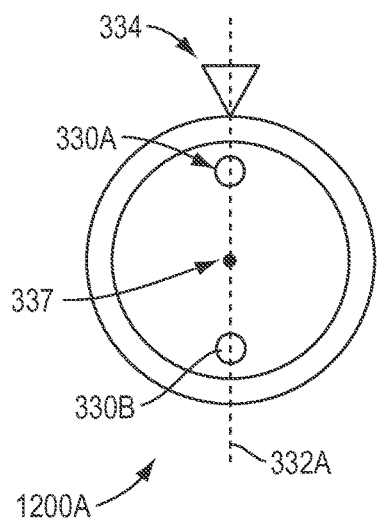
FIG. 12A shows a schematic cross-sectional view of a wrist of a surgical instrument, according to an exemplary embodiment.

Various exemplary embodiments in accordance with the present disclosure contemplate other initial positions actuation element twist configurations than those shown and discussed with reference to the exemplary embodiment of FIGS. 10A, 10B, and 11. With reference to FIG. 12A, a schematic cross-sectional view is shown of a joint of an exemplary embodiment of a wrist. The joint 1200A depicted in the exemplary embodiment of FIG. 12A may be an A type joint similar to the exemplary embodiment of FIG. 10A, except that the initial positions of actuation elements 330A, 330B in joint 1200A are aligned with bend axis 332A. Actuation elements 330A, 330B may be used, for example, to actuate an end effector (such as end effector 252 of the exemplary embodiment of FIG. 8) or to actuate another component of an instrument, such as, for example, a wrist. According to an exemplary embodiment, actuation elements 330A, 330B may follow a twisted path so that actuation of actuation elements 330A, 330B does not result in an inverted motion, such as when actuation elements 330A, 330B are used to actuate a wrist.

Figure 12B:
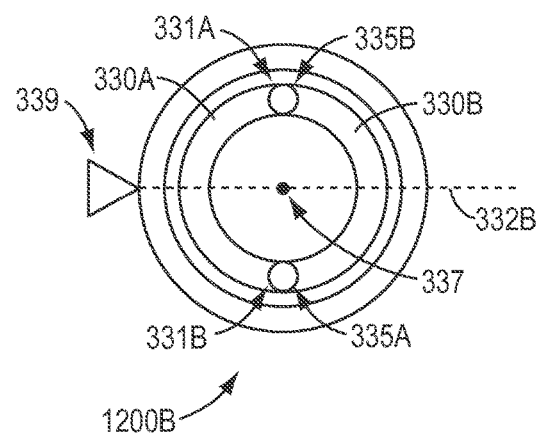
FIG. 12B shows a schematic cross-sectional view of a wrist of a surgical instrument, according to an exemplary embodiment.
Figure 13:
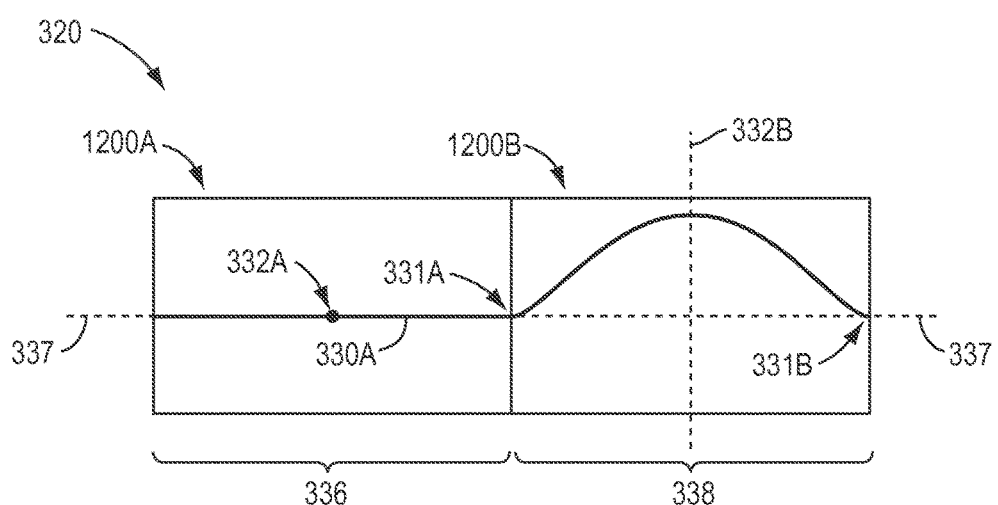
FIG. 13 shows a top view schematically illustrating the shape of an actuation element along a wrist.
Figure 15:
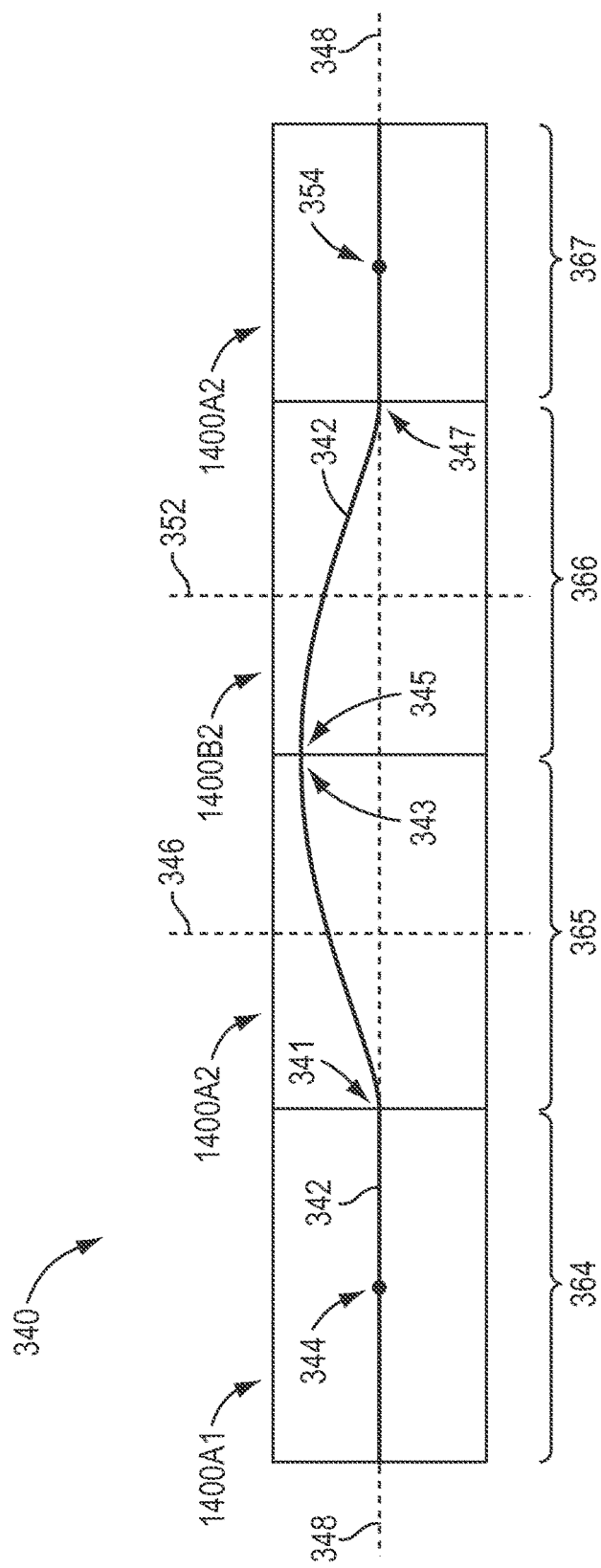
FIG. 15 shows a top view schematically illustrating the shape of an actuation element along a wrist.
Figure 16:
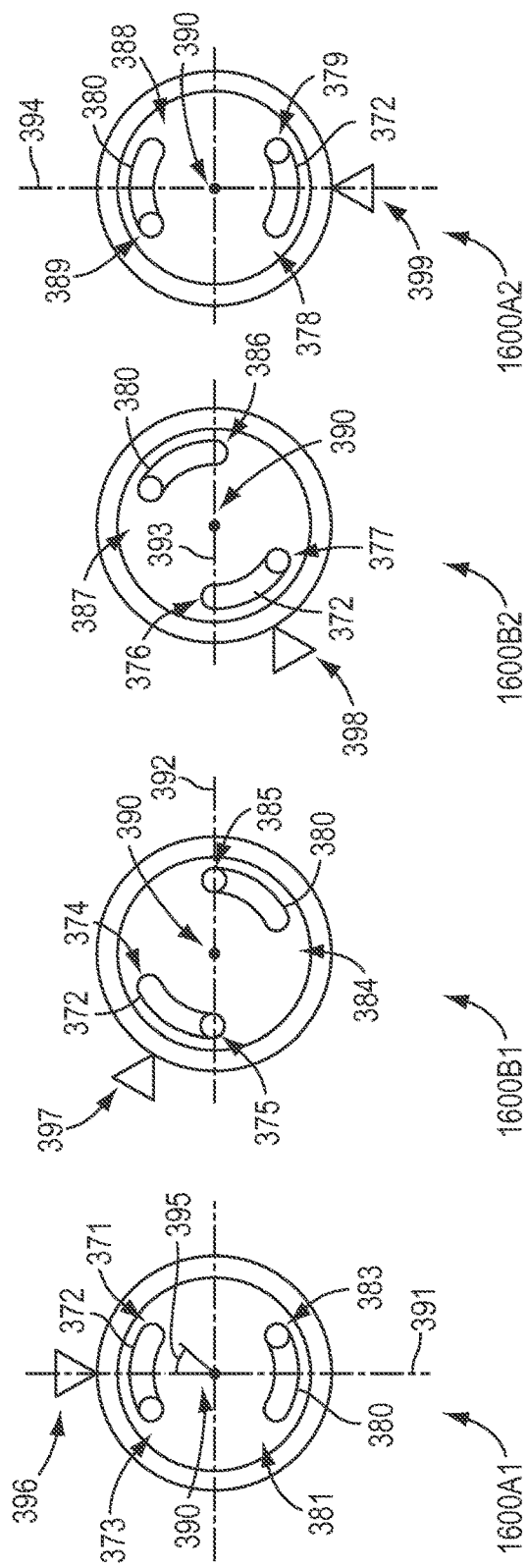
FIG. 16A shows a schematic cross-sectional view of a wrist of a surgical instrument, according to an exemplary embodiment.
FIG. 16B shows a schematic cross-sectional view a wrist of a surgical instrument, according to an exemplary embodiment.
FIG. 16C shows a schematic cross-sectional view of a wrist of a surgical instrument, according to an exemplary embodiment.
FIG. 16D shows a schematic cross-sectional view of a wrist of a surgical instrument, according to an exemplary embodiment.

As shown in FIG. 12A and in FIG. 13, the latter of which is a top schematic view of a wrist 320 including the joints depicted in FIGS. 12A and 12B but showing only the twist of actuation element 330A, actuation element 330A does not have a twist along the length 336 of joint 1200A relative to the longitudinal neutral axis 337. As discussed above with regard to FIG. 11, axis 337 may be a centerline for wrist 320 and in addition may be a centerline for the twisted path of actuation elements 330A, 330B. Thus, the average angular position 334 of actuation elements 330A, 330B over a length 336 of joint 1200A (shown schematically in FIG. 13) is lined up with bend axis 332A (i.e., bend axis 332A passes through actuation elements 330A, 330B). As a result, actuation elements 330A, 330B are already length conservative in joint 1200A and need not be twisted in that joint. However, in joint 1200B, the respective initial positions 331A, 335A of actuation elements 330A, 330B are offset from bend axis 332B. For example, initial positions 331A, 335A of actuation elements 330A, 330B may be offset by approximately 90° from bend axis 332B in joint 1200B.

To achieve length conservation of actuation elements 330A, 330B across joint 1200B, actuation elements 330A, 330B may be twisted an angular extent of 180° to respective subsequent positions 331B, 335B (i.e., follow a twisted path over an angular extent of 180° about centerline 337). As a result, an approximately equal amount of each of actuation elements 330A, 330B is on either side of bend axis 332B in joint 1200B (e.g., the top and bottom side in the cross-section of joint 1200B in FIG. 13B). This is also demonstrated by the average angular position 339 of actuation elements 330A, 330B over a length 338 of joint 1200B (shown schematically in FIG. 13), which aligns with bend axis 332B (i.e., bend axis 332B passes through average angular position 339 of actuation elements 330A, 330B). Thus, actuation elements 330A, 330B may follow a twisted path having an angular extent of 180° over the length of wrist 320, similar to the exemplary embodiment of FIGS. 10A, 10B, and 11, but with no twisting occurring over the length of one joint (e.g., joint 1200A) and all of the twisting occurring over the length of another joint (e.g., joint 1200B). Further, actuation elements 330A, 330B may be twisted in this manner to make each of actuation elements 330A, 330B length conservative across each of joints 1200A and 1200B.

Wrists can be configured to include any number of joints with varying bend axes directions for each joint. Some nonlimiting examples contemplated as within the scope of the present disclosure include a wrist having one or more multiples of wrists 310 and/or 320 of the exemplary embodiments of FIGS. 10A-13, with the length of actuation elements being substantially conserved over the total length of the wrist. For instance, a wrist could include two consecutive wrist devices each configured according to either of the exemplary embodiments of FIGS. 10A-13. Such a wrist can include, for example, in sequence, a first A joint, a first B joint, a second A joint, and a second B joint (i.e., the wrist would be an ABAB type of wrist). To achieve length conservation of actuation elements extending across the length of the wrist, the actuation elements may extend along a twisted path having an angular extent of 360° over the length of the wrist, which is twice the angular extent for each of wrist 310, 320 of the exemplary embodiments of FIGS. 10A-13. Conversely, a wrist including two consecutive wrist devices (e.g., an ABAB type of wrist) may be simplified to a wrist including a single wrist, such as the wrists 310 and/or 320 of the exemplary embodiments of FIGS. 10A-13 (e.g., an AB type of wrist). Similarly, an AABB type of wrist could be simplified to an AB wrist.

Various exemplary embodiments in accordance with the present disclosure contemplate various bending axis patterns of a wrist and twist configurations for actuation elements. Although wrist configurations may include only joints with two bending axes, as shown in FIGS. 8 and 10A-13, other wrist configurations may be used, such as the ABBA wrist of the exemplary embodiment of FIG. 9.

Turning to FIGS. 14A-14D, cross-sectional views are shown of joints of a wrist that includes four joints 1400A1, 1400B1, 1400B2, 1400A2, according to an exemplary embodiment. For instance, the wrist may be constructed according to the exemplary embodiment of the ABBA wrist of FIG. 9 and the respective cross-sectional views of joints A1, B1, B2, and A2 in FIGS. 14A-14D may be views along lines A1-A1, B1-B1, B2-B2, A2-A2 in FIG. 9. Thus, the cross-sections of joints 1400A1, 1400B1, 1400B2, 1400A2 in FIGS. 14A-14D respectively represent four different joints of the wrist 340 schematically shown in the exemplary embodiment of FIG. 15, with joint 1400A1 having a bending axis 344 and a length 364 (schematically shown in FIG. 15), joint 1400B1 having a bending axis 346 and a length 365 (schematically shown in FIG. 15), joint 1400B2 having a bending axis 352 and a length 366 (schematically shown in FIG. 15), and joint 1400A2 having a bending axis 354 and a length 367 (schematically shown in FIG. 15). Further, wrist 340 has a longitudinal neutral axis 348, as shown in FIGS. 14A-14D and 15. Axis 348 may be a centerline for wrist 340 and may further be a centerline for the twisted path of actuation elements 342, 350. Actuation elements 342, 350 may be used, for example, to actuate an end effector, or to actuate another component of an instrument, such as, for example, a wrist. According to an exemplary embodiment, actuation elements 342, 350 may follow a twisted path so that actuation of actuation elements 342, 350 does not result in an inverted motion (e.g., joints 300 and 306 in FIG. 9 do not bend in different directions about axes 290 and 296, and joints 302 and 304 do not bend in different directions about axes 292 and 294), such as when actuation elements 342, 350 are used to actuate a wrist. According to an exemplary embodiment, the twist of actuation elements 342, 350 for each of joints 1400A1, 1400B1, 1400B2, 1400A2 may be centered about the respective bending axes 344, 346, 352, 354, with the twisted path extending in a substantially equal amount on either side of the respective bending axes 344, 346, 352, 354.

The angular extent of twist of actuation elements 342, 350 extending across wrist 340 is such that actuation elements 342, 350 are length conservative over the length of wrist 340. In joint 1400A1, both of actuation elements 342, 350 are aligned with bend axis 344 (i.e., bend axis 344 passes through actuation elements 342, 350) and thus have an average angular position 356 across the length 364 of joint 1400A1 that is aligned with bend axis 344. Thus, both of actuation elements 342, 350 do not substantially change in length in joint 1400A1 and are not twisted in that joint. In joint 1400B1, actuation element 342 has an initial position 341 as it enters from joint 1400A1 that has an approximately 90° angle 349 to bend axis 346. Actuation element 350 also has an initial position 351 as it enters from joint A1 that is at an approximately 90° angle to bend axis 346.

In the exemplary embodiment of FIG. 14B, actuation elements 342, 350 may be twisted 90° (i.e., follow a twisted path having an angular extent of 90° about the centerline 348) in joint 1400B1 to respective subsequent positions 343, 353, providing actuation elements 342, 350 with an average angular position 358 across the length 365 of joint 1400B1. As shown in the exemplary embodiment of FIG. 14B, average angular position 358 is not aligned with bend axis 346, resulting in a positive or negative change in length for actuation elements 342, 350 in joint 1400B1. In joint 1400B2, actuation element 342 has an initial position 345 after entering from joint 1400B1 at an angle 359 of 90° relative to bend axis 352 and actuation element 350 has an initial position 355 at 90° to bend axis 352, as shown in FIG. 14C. Actuation elements 342, 350 are twisted 90° (i.e., follow a twisted path having an angular extent of 90° about centerline 348) in joint 1400B2 to provide an average angular position 360 across the length 366 of joint 1400B2, resulting in a positive or negative change in lengths for each of actuation elements 342, 350 in joint 1400B2.

However, the twists of actuation elements 342, 350 in joints 1400B1, 1400B2 are on opposite sides of bend axes 346, 352, as indicated by average angular positions 358, 360 across the respective lengths 365, 366 of joints 1400B1, 1400B2, and the changes in length of actuation elements 342, 350 substantially cancel one another out. Further, actuation elements 342, 350 are aligned with bend axis 354 (i.e., bend axis 354 passes through actuation elements 342, 350) in joint 1400A2, as indicated by average angular position 362 of actuation elements 342, 350 across the length 367 of joint 1400A2. As a result, actuation elements 342, 350 are twisted 180° (i.e., the twisted path has an angular extent of 180° about centerline 348) through the entire length of wrist 340 (i.e., 90° through each of joints 1400B1 and 1400B2). Further, because the twists of actuation elements 342, 350 relative to bend axes 346, 352 of joints 1400B1, 1400B2 are on opposite sides of bend axes 346, 352, actuation elements 342, 350 do not experience a substantial change of length in joints 1400A1, 1400A2, and any positive or negative change of length of actuation elements 342, 350 in joint B1 is offset by a corresponding negative or positive change in length of actuation elements 342, 350 in joint 1400B2, and vice versa. Thus, each actuation element 342, 350 is length conservative over the entire length of wrist 340.

The present disclosure contemplates other configurations for wrists having more than two joints. Turning to FIGS. 16A-16D, cross-sectional views are shown of joints 1600A1, 1600B1, 1600B2, 1600A2 of a wrist. Wrist 370 may be constructed, for example, according to the exemplary embodiment shown in FIG. 9 and the cross-sectional views of joints 1600A1, 1600B1, 1600B2, and 1600A2 in FIGS. 16A-16D may be views along lines A1-A1, B1-B1, B2-B2, and A2-A2 for the exemplary embodiment of an ABBA wrist in FIG. 9.

Figure 17:
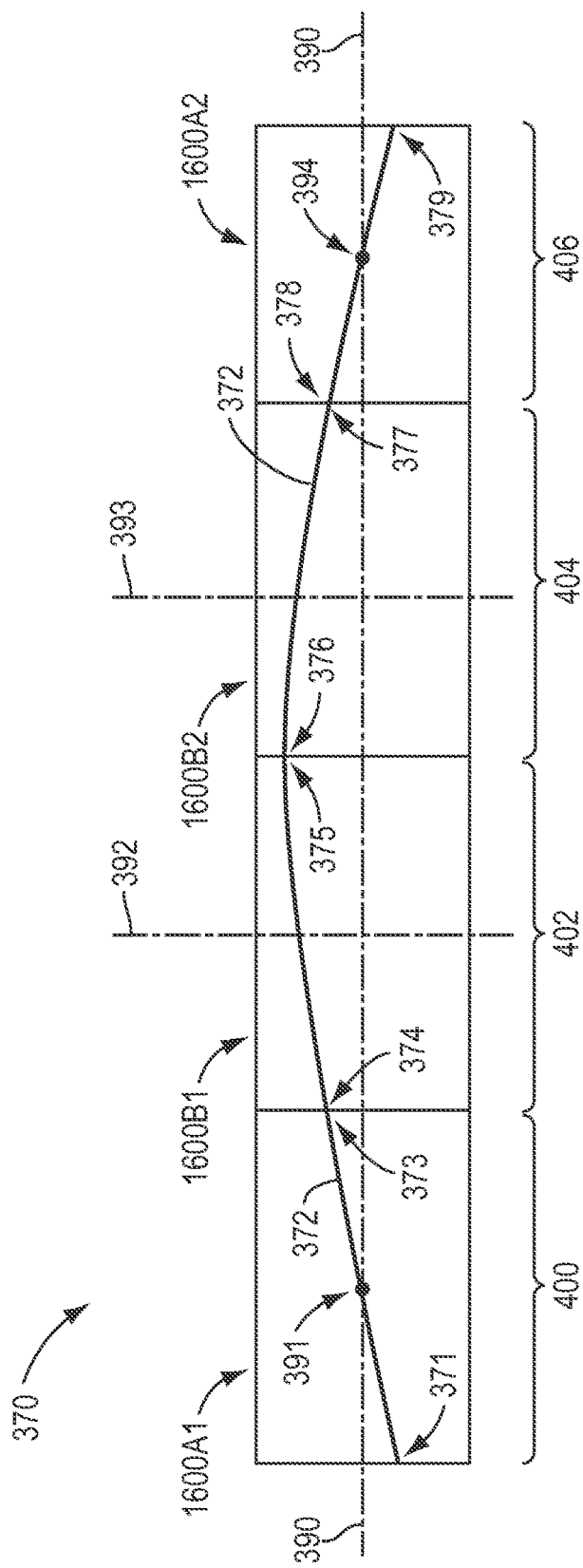
FIG. 17 shows a top view schematically illustrating the shape of an actuation element along a wrist.

According to an exemplary embodiment, joint 1600A1 having a bending axis 391 and a length 400 (shown schematically in the exemplary embodiment of FIG. 17, which shows the entire wrist 370 and includes the joints depicted in FIGS. 16A-16D), joint 1600B1 having a bending axis 392 and a length 402 (shown schematically in FIG. 17), joint 1600B2 having a bending axis 393 and a length 404 (shown schematically in FIG. 17), and joint 1600A2 having a bending axis 394 and a length 406 (shown schematically in FIG. 17). Further, wrist 370 may include a longitudinal neutral axis 390 that extends through joints 1600A1, 1600B1, 1600B2, 1600A2, as shown in FIGS. 16A-16D and 17. Axis 390 may be a centerline for wrist 370 and may also be a centerline for the twisted path of actuation elements 372, 380. Actuation elements 372, 380 may be used, for example, to actuate an end effector, or to actuate another component of an instrument, such as, for example, a wrist. According to an exemplary embodiment, actuation elements 372, 380 may follow a twisted path so that actuation of actuation elements 372, 380 does not result in an inverted motion (e.g., joints 300 and 306 in FIG. 9 do not bend in different directions about axes 290 and 296, and joints 302 and 304 do not bend in different directions about axes 292 and 294), such as when actuation elements 372, 380 are used to actuate a wrist.

In the exemplary embodiment of FIGS. 16A-16D and 17, actuation elements 372, 380 may be initially offset and not aligned from bend axis 391 in joint 1600A1. For instance, actuation elements 372, 380 may initially be at an angle 395 of approximately 30° to bend axis 391. To address this, actuation elements 372, 380 may be twisted 60° (i.e., follow a twisted path having an angular extent of 60° about centerline 390) from respective initial positions 371, 381 to subsequent positions 373, 383 along the length 400 of joint 1600A1 so that actuation elements 372, 380 are length conservative in joint 1600A1. Thus, the average angular position 396 of actuation elements 372, 380 across the length 400 of joint 1600A1 aligns with bend axis 391 (bend axis 391 passes through average angular position 396 of actuation elements 372, 380).

Similarly, actuation elements 372, 380 may be twisted 60° (i.e., follow a twisted path having an angular extent of 60° about centerline 390) in joint 1600B1 from respective initial positions 374, 384 to subsequent positions 375, 385; twisted 60° (i.e., follow a twisted path having an angular extent of 60° about centerline 390) in joint 1600B2 from respective initial positions 376, 386 to subsequent positions 377, 387;

and twisted 60° (i.e., follow a twisted path having an angular extent of 60° about centerline 390) in joint 1600A2 from respective initial positions 378, 388 to subsequent positions 379, 389. Similar to joint A1, the average angular position 399 of actuation elements 372, 380 across the length 406 of joint 1600A2 aligns with bend axis 394 so that actuation elements 372, 380 are substantially length conservative across joint 1600A2. Actuation elements 372, 380 are not length conservative over the lengths 402, 404 of each of joints 1600B1, 1600B2. However, when taken in total over the combined lengths 402 and 404 of joints 1600B1 and 1600B2, actuation elements 372, 380 are substantially lengths conservative over the combination of joints 1600B1 and 1600B2. This is indicated by the average angular position 397 of actuation elements 372, 380 across the length 402 of joint 1600B1 and the average angular position 398 of actuation elements 372, 380 across the length 404 of joint 1600B2 which are on opposite sides of their respective bending axes 393 and 393. Thus, actuation elements 372, 380 may be twisted a total amount of 240° (i.e., have a twisted path having an angular extent of 240° about centerline 390) over the entire length of wrist 370 (i.e., twisted 60° across each of the lengths of joints 1600A1, 1600B1, 1600B2, 1600A2).

To extend an actuation element along a twisted path, as described in the exemplary embodiments above, various exemplary embodiments contemplate one or more structures that guide one or more actuation elements along a twisted path. One or more structures may provide support to the actuation element along its length to minimize or reduce buckling of the actuation element as the actuation element extends along the twisted path according to the exemplary embodiments described herein, such as the exemplary embodiments of FIGS. 10A-17.

Figure 18:
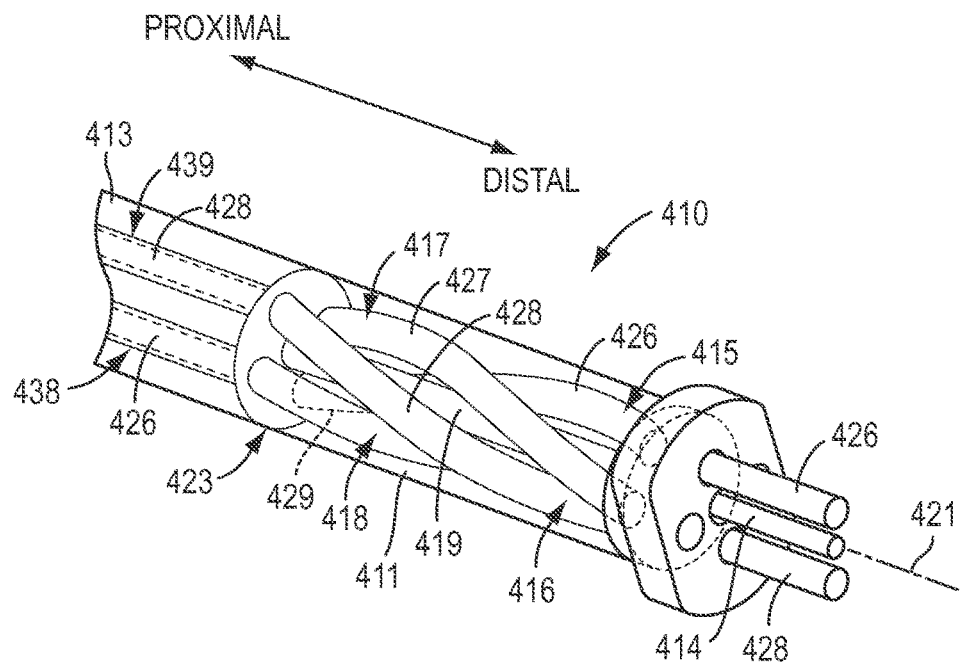
FIG. 18 shows a perspective view of a distal portion of a surgical instrument shaft, according to an exemplary embodiment.

Turning to FIG. 18, a distal portion of a surgical instrument is shown, including an actuation element support 410 located at a distal end of an instrument shaft, such as the shaft 251 of the exemplary embodiment of FIG. 8. According to an exemplary embodiment, a first portion 411 of actuation element support 410 may include twisted passages 415, 416 that provide a twisted path for actuation elements 426, 428 that extend through passages 415, 416 of first portion 411. Actuation elements 426, 428 may extend out of a proximal end 423 of support 410 and into a second portion 413 of actuation element support 410, which includes substantially straight passages 438, 439 through which actuation elements 426, 428 may extend, as shown in the exemplary embodiment of FIG. 18. Although only two passages 438, 439 are depicted in the exemplary embodiment of FIG. 18 for ease of illustration, second portion 413 of actuation element support 410 may include the same number of passages as first portion 411. According to an exemplary embodiment, the passages of second portion 413 may be joined to the passages of first portion 411 so that any actuation elements extending through the passages of second portion 413 extend through corresponding passages in first portion 411.

According to an exemplary embodiment, support 410 may further include a central passage 419 through which an actuation element 414 may extend. Central passage 419 may extend along a longitudinal centerline 421 of instrument so that any member extending through central passage 419, such as actuation element 414 or a flux conduit, does not experience a substantial change in length when support 410 is bent. Centerline 421 may also be a centerline of support 410, according to an exemplary embodiment. Actuation element 414 may be used, for example, to actuate an end effector, such as, for example, a cutting blade. The actuation elements of the various exemplary embodiments described herein that are radially offset from a neutral axis or centerline are not limited to actuating an end effector or wrist, but may be used to actuate other instrument components. For example, the actuation elements of the various exemplary embodiments described herein that are radially offset from a neutral axis or centerline may actuate a second wrist distal to actuation element support 410, or other instrument component. In another example, actuation element 414 may be used to actuate an end effector, while actuation elements 426, 428 are used to actuate the wrist that end effector is connected to. According to another example, a flux conduit may extend through central passage 419 instead of actuation element 414.

One or more actuation elements may extend from actuation element support 410 and connect to a device used to actuate an instrument component. As shown in the exemplary embodiment of FIG. 19, actuation element support 440 may include a central lumen 442, such as for a flux conduit or actuation element 414 (which may further extend through a lumen 424 of connector 420), lumens 446 for actuation elements 426, 428, and two additional lumens 444 that may be used for other actuation elements or flux conduits. According to an exemplary embodiment, actuation elements 426, 428 and connector 420 may form a push/pull actuation element that actuates an end effector, such as when actuation elements 426, 428 and connector are pushed or pulled along direction 435. Turning to FIG. 20, a side view of an end effector 434 is shown in a closed configuration, with projections 422 of connector 420 extending through a slot 437 of end effector 404. When actuation elements 426, 428, connector 420, and projection 422 are pushed in direction 425, projection 422 moves through slot 437 and forces end effector 434 into an open configuration, as shown in FIGS. 20 and 21.

Although actuation elements 426, 428 may be used as push/pull actuation elements, actuation elements 426, 428 may instead be used as a pull/pull actuation element. For instance, actuation elements 426, 428 may be attached to a proximal end 409 of end effector 404 without using connector 420 so that end effector 404 may be opened by pulling on one of actuation elements 426, 428 and closed by pulling the other of actuation elements 426, 428.

According to an exemplary embodiment, an actuation element support may be positioned in a surgical instrument so that the location of the support corresponds to the location of a wrist because the wrist can bend, which could cause actuation elements extending through the wrist to change in length. Because central passage 419 is located along longitudinal centerline 421 of instrument, actuation elements 426, 428 and their respective passages 415, 416 are radially offset from centerline 421. Thus, when wrist 430 is actuated to bend the instrument, such as to position end effector 434 in a desired location, actuation elements 426, 428 might experience a change in length. However, support 440 imparts a twisted path to actuation elements 426, 428, such as according to the exemplary embodiments of FIGS. 10A-17, so that actuation elements 426, 428 do not experience a substantial change in length over the length of wrist 430.

Passages 415, 416 are twisted 180° in the exemplary embodiment of FIG. 18 but other configurations of twist may be used, as described in the exemplary embodiments of FIGS. 10A-17. Actuation element support 410 may include various numbers of passages to provide a twisted path for one or more actuation elements. For instance, actuation element support 410 may include one passage, two passages, three passage, or four or more passages. For instance, actuation element support 410 may include a third passage 417 and a fourth passage 418, which may be used for additional actuation elements or for flux conduits 427, 429, such as electrical conductors to provide electrical energy to an end effector (not shown).

As shown in the exemplary embodiment of FIG. 18, actuation element support 410 may have a solid, single-piece construction with passages 415-418 formed through the length of support 410. According to an exemplary embodiment, actuation element support 410 may be manufactured, for example, by extruding a polymer material into a substantially cylindrical shape with twisted passages 415-418 formed through the length of the polymer material. However, other manufacturing methods may be utilized to provide a support 410 having one or more twisted passages radially offset from and twisting about a centerline 421 of support 410. Thus, support 410 may guide one or more actuation elements along a twisted path and provide support to the actuation elements to minimize or eliminate buckling of the actuation elements. For instance, when an actuation element is used as a push/pull actuation element and the actuation element is pushed, support 410 may reduce or eliminate buckling of the actuation element.

In various exemplary embodiments, support 410 may be flexible to promote bending of support 410 when a wrist that support 410 extends through is actuated. Support 410 may be made from, for example, a polymer material to provide a relatively low coefficient of friction. According to an exemplary embodiment, support 410 may be made of, for example, polyether block amide (PEBAX), fluorinated ethylene propylene (FEP), and other polymer materials having a relatively low coefficient of friction familiar to one skilled in the art. In addition, actuation elements extending through support 410 may be coated with a material to minimize friction between the actuation elements and support 410. For example, actuation elements may be coated with polytetrafluoroethylene (PTFE) or other lubricious material familiar to one skilled in the art.

Figure 19:
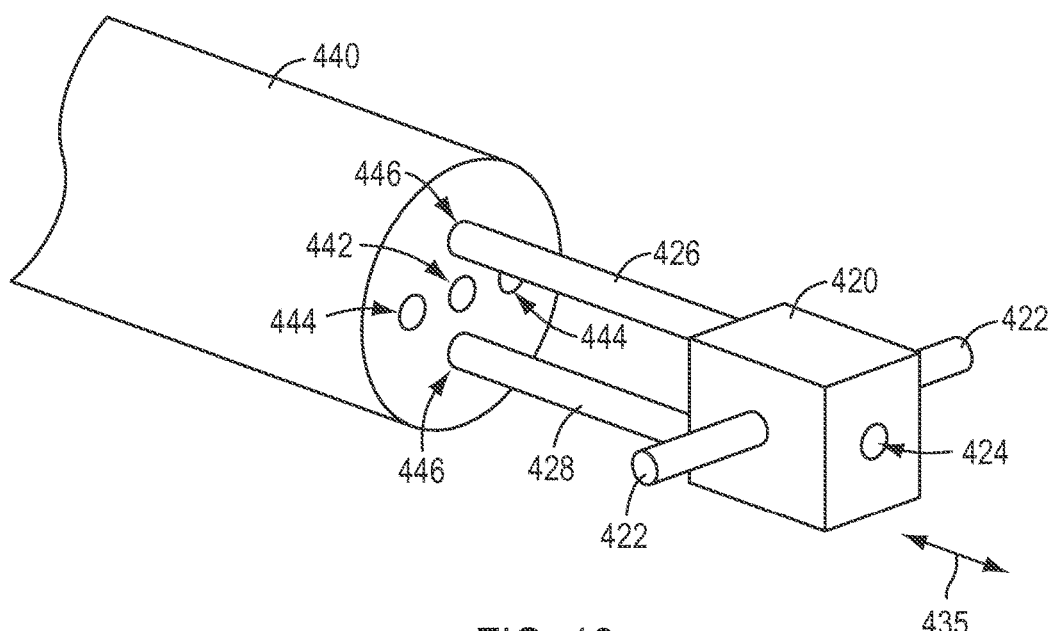
FIG. 19 shows a schematic perspective view of an actuation element support and push/pull actuation element, according to an exemplary embodiment.
Figure 20:
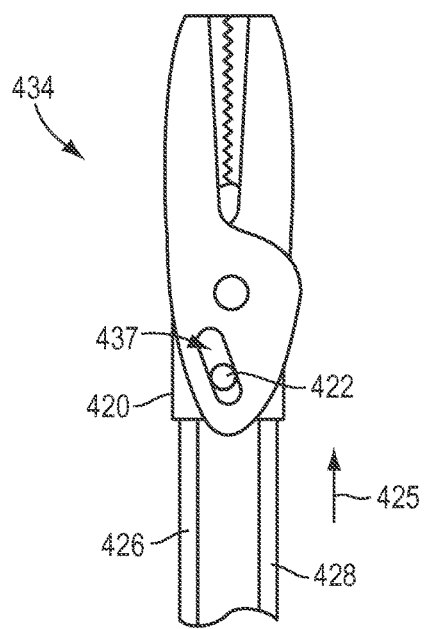
FIG. 20 is a side view of an end effector in a closed configuration, according to an exemplary embodiment.
Figure 22:
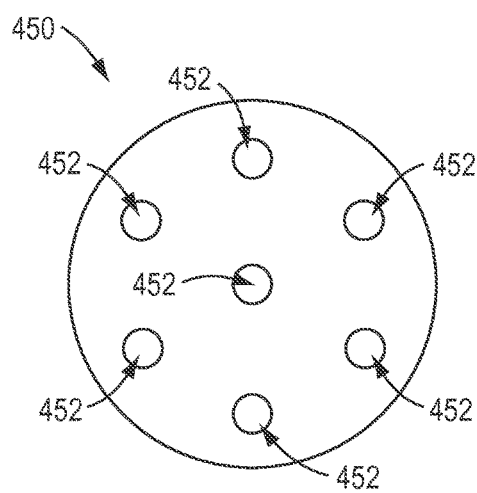
FIG. 22 shows an end view of end face of an actuation element support, according to an exemplary embodiment.
Figure 23:
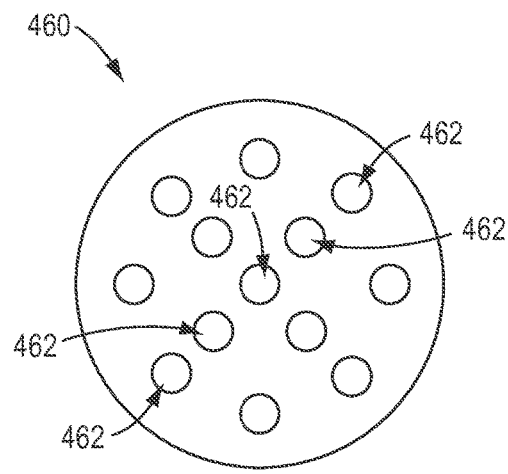
FIG. 23 shows an end view of end face of an actuation element support, according to an exemplary embodiment.

As shown in the exemplary embodiment of FIG. 19, an actuation element support 440 may include five lumens 442, 444, 446. However, a surgical instrument, including an actuation element support, is not limited to only five members and a greater or lesser number of lumens may be used in an instrument. For instance, an actuation element support 450 may include seven lumens 452 as shown in the exemplary embodiment of FIG. 22. In addition, lumens of an actuation element support need not be arranged as a single ring of lumens around a central lumen, as in the exemplary embodiment of FIG. 22. Instead, lumens 462 of a support 460 may be arranged in a plurality of concentric rings around a central lumen, as shown in the exemplary embodiment of FIG. 23.

Figure 24:
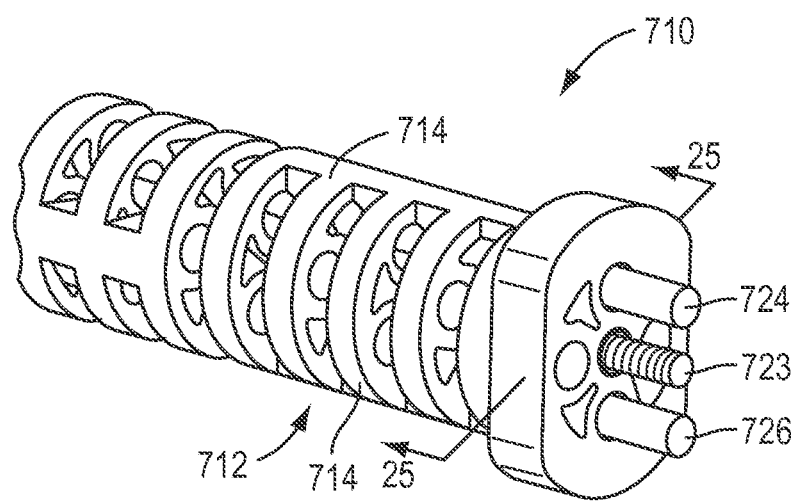
FIG. 24 is a perspective view of components of a distal portion of a surgical instrument, according to an exemplary embodiment.
Figure 25:
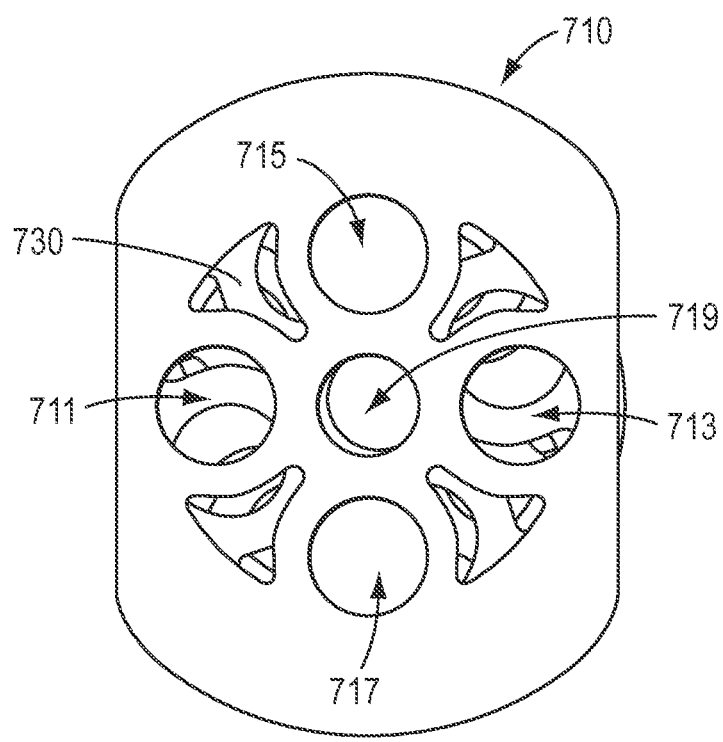
FIG. 25 is a cross-sectional view along line 25-25 of FIG. 24.

As discussed above with regard to the exemplary embodiment of FIG. 18, an actuation element support may have a single-piece construction. For instance, the support may be a single piece that has been extruded. Such an extrusion may have a solid, substantially continuous outer surface without grooves. However, other configurations and constructions may be used for an actuation element support. For instance, an actuation element support may include one or more areas of material weakness to enhance the flexibility of the support. Turning to FIG. 24, an exemplary embodiment of an actuation element support 710 is shown, with actuation elements 724, 726 extending through support 710. To enhance the flexibility of support 710, such as when support 710 is bent by a wrist, support 710 may include one or more areas of material weakness, such as grooves 712, as shown in the exemplary embodiment of FIG. 24. According to an exemplary embodiment, support 710 may be formed as an extrusion with lumens formed through support 710, similar to the exemplary embodiment of FIG. 19, and then have grooves 712 cut into the extrusion to provide vertebrae 714 separated by grooves 712. As shown in FIG. 25, which is a cross-sectional view along line 25-25 in FIG. 24, support 710 may include five lumens 711, 713, 715, 717, 719, similarly to the exemplary embodiment of FIG. 19. However, support 710 may include other numbers of lumens and may include the lumen configurations of the exemplary embodiments of FIGS. 22 and 23. According to an exemplary embodiment, support 710 may include other areas of weakness besides grooves. For instance, support 710 may include apertures 730, which may be formed in vertebrae 714, to provide additional areas of weakness and enhanced flexibility to support 710.

Figure 26:
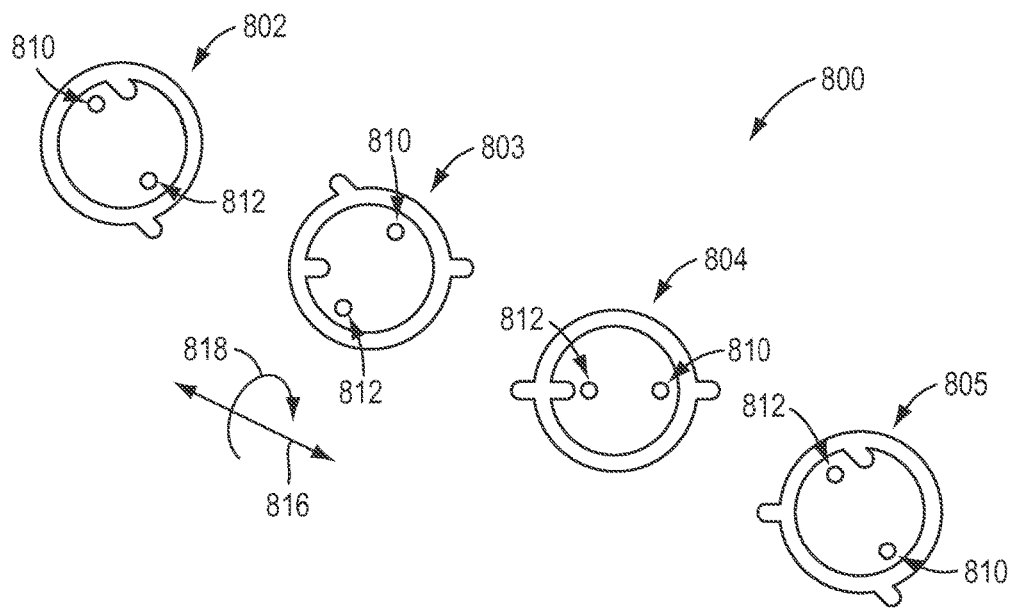
FIG. 26 is an exploded view of an actuation element support, according to an exemplary embodiment.

According to an exemplary embodiment, actuation elements may be supported and shaped into a twisted path by components other than the single piece constructions of FIGS. 18, 24, and 25. Turning to FIG. 26, an exploded view is shown of an actuation support 800 that is formed by a plurality of separate links 802-805, according to an exemplary embodiment. Links 802-805 may include one or more passages 810, 812 for actuation elements (not shown). As shown in the exemplary embodiment of FIG. 26, links 802-805 may be rotated about a longitudinal axis 816 (i.e., centerline) of support 800 in direction 818 to impart a twist to actuation elements passing through passages 810, 812. Thus, passages 810, 812 of links 802-805 may have a different angular position with respect to centerline 816 from one link to another. Links 802-805 may impart other amounts of twist, such as the amounts of twist discussed in the exemplary embodiments of FIGS. 10A-17. In addition, links 802-805 may include other numbers of lumens and may include the lumen configurations of the exemplary embodiments of FIGS. 22 and 23.

Figure 27:
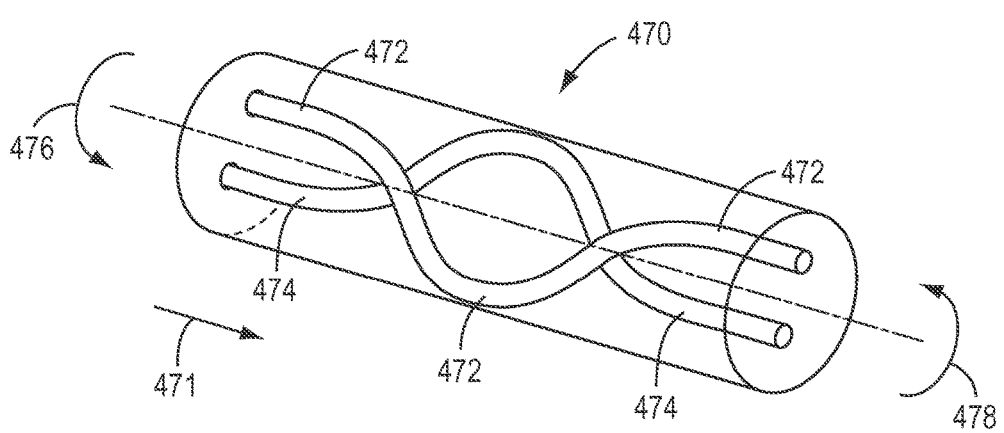
FIG. 27 is a schematic perspective view of an actuation element support, according to an exemplary embodiment.

As shown in the exemplary embodiment of FIG. 18, lumens 415-418 of an actuation element support 410 may twist in one direction from one end of support 410 to another. However, actuation element supports are not limited to such a twisted configuration and may instead include lumens that twist in more than one direction. Turning to FIG. 27, an exemplary embodiment of an actuation element support 470 is shown that includes lumens 472, 474 that twist in a first direction 476 along support 470 in direction 471 and then reverse to twist along direction 478. Further, the amount of twist may be constant along the length of a support or may vary by increasing or decreasing along the length of a support.

Figure 28:
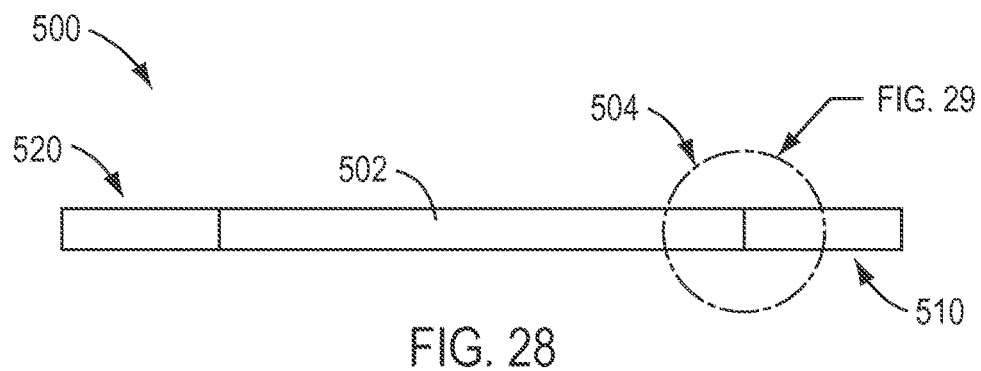
FIG. 28 is a side view of an exemplary embodiment of an actuation element that includes a rigid section.
Figure 29:
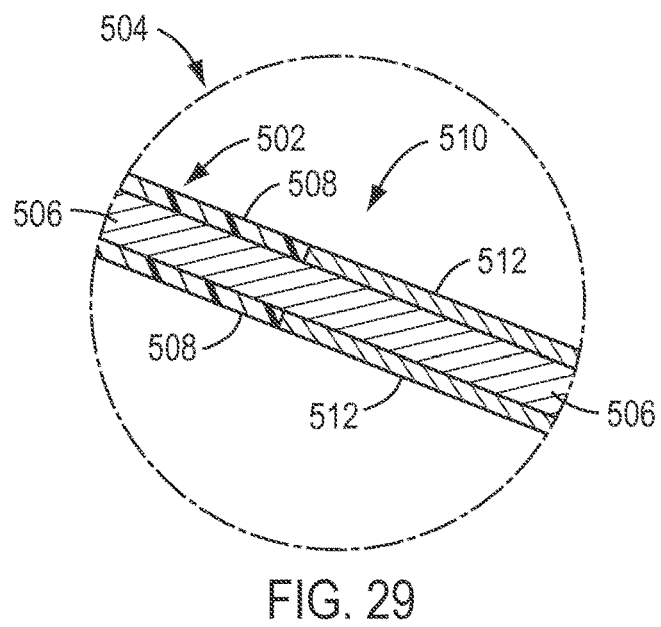
FIG. 29 is an enlarged view of a portion of FIG. 28.

As discussed above, an actuation element support may function both to guide an actuation element along a twisted path and to support the actuation element to minimize or prevent buckling of the actuation element. Other structures may be provided to enhance the support of an actuation element and its buckling strength, which may be used with an actuation element support. Turning to FIG. 28, an exemplary embodiment of an actuation element 500 is shown that includes a rigid section 510 at a distal end of an unsupported section 502 of actuation element 500. As shown in FIG. 29, which is an enlarged view of portion 504 in FIG. 28, actuation element 500 may include a wire or cable 506 that extends into rigid section 510. Wire or cable 506 may be, for example, one of actuation elements 426, 428 of the exemplary embodiment of FIG. 18. Rigid section 510 may include a rigid cylinder 512 fitted over wire or cable 506.

Rigid cylinder 512 may made of, for example, steel, such as stainless steel. Rigid cylinder 512 may be connected to wire or cable 506 via, for example, crimping cylinder 512 to wire or cable 506.

According to an exemplary embodiment, unsupported section 502 of wire or cable 506 may include a coating 508. Coating 508 may be used, for example, to provide wire or cable 506 with a smooth surface having a lower coefficient of friction than wire or cable 506. Coating 508 may be made of polymer, such as a thermoplastic. According to an exemplary embodiment, coating 508 may be made of, for example, PTFE, ethylene tetrafluoroethylene (ETFE), silicone, or other coating materials familiar to one skilled in the art. According to an exemplary embodiment, coating 508 may have a thickness that is substantially the same as the thickness of cylinder 512, as shown in FIG. 29.

Figure 30:
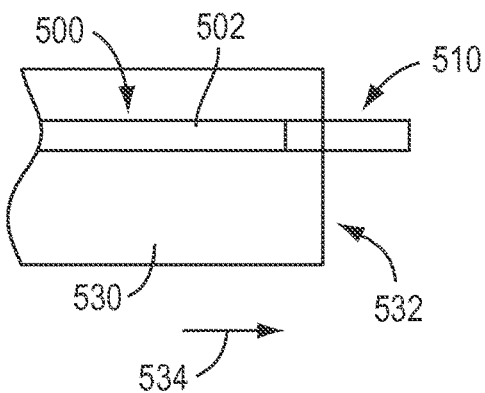
FIG. 30 is a side cross-sectional view of an actuation element support and actuation element, according to an exemplary embodiment.

By providing actuation element 500 with a rigid section 510, the buckling strength of actuation element 500 may be enhanced. For instance, when actuation element 500 is inserted through an actuation element support 530 (e.g., actuation element support 410 of the exemplary embodiment of FIG. 18), actuation element 500 may be pushed along direction 534, causing a distal end of actuation element 500 to extend beyond a distal end 532 of actuation element support 530, as shown in the exemplary embodiment of FIG. 30. Because actuation element 500 includes a rigid section 510, the portion of actuation element 500 that extends beyond the distal end 532 of actuation element support 530 may have enhanced buckling strength. For instance, a surgical instrument may be configured so that when actuation element 500 is pushed along direction 534, only the rigid section 510 of actuation element 500 extends beyond distal end 532 of actuation element support 530, as shown in FIG. 30, with the unsupported section 502 of actuation element 500 remaining within actuation element support 530.

According to an exemplary embodiment, a proximal end of actuation element 500 may also include a rigid section 520, as shown in FIG. 28, although other exemplary embodiments may lack a rigid section at a proximal end of an actuation element. The rigid section 520 at proximal end may be configured according to the rigid section 510 of the exemplary embodiment of FIG. 29. According to an exemplary embodiment, rigid section 520 may extend past a proximal end of an actuation element support, such as when actuation element is pulled, similar to the exemplary embodiment of FIG. 30.

Figure 31:
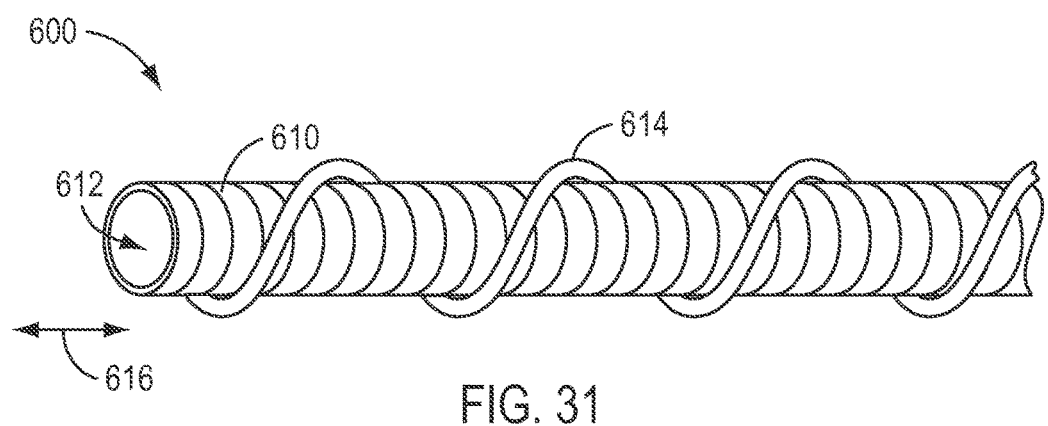
FIG. 31 is a partial perspective view of an exemplary embodiment of a flexible shaft.

Another structure that may be used to support an actuation element is a flexible shaft. Turning to FIG. 31, an exemplary embodiment of a flexible shaft 600 is shown, which includes a compression member 610 and a tension member 614. Flexible shaft 600 may be used to support an actuation element, with flexible shaft 600 extending through at least a portion of an actuation element support, similar to the exemplary embodiment of FIG. 30. Compression member 610 may have a central lumen 612 for an actuation element to pass through. Compression member 610 may be, for example, a spring including windings that compress against one another when a compressive force is applied along a longitudinal axis 616 of flexible shaft 600. Tension member 614 may be a wire or cable attached to compression member 610, such as on the exterior of compression member 610, to resist tensile forces applied along axis 616 or bending forces applied to flexible shaft 600. In other words, flexible shaft 600 may be a combination of a compression member 610 that resists compression, which could otherwise compress tension member 614 if compression member 610 were not present, and a tension member 614 that resists tension and bending, which could otherwise pull apart compression member 610.

Figure 32:
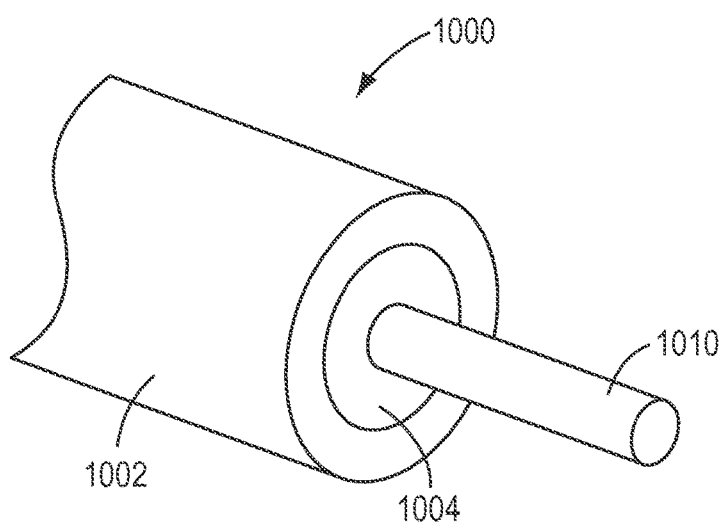
FIG. 32 is a perspective end view of an actuation support element including coaxial flexible tubes and an actuation element, according to an exemplary embodiment.

According to an exemplary embodiment, an actuation element support may include a plurality of flexible shaft layers. For example, an actuation element support may include multiple flexible shafts layered over one another, such as by providing multiple layers of the flexible shaft 600 of the exemplary embodiment of FIG. 31 over one another. The various layers of the flexible shafts may be coaxial to one another. For example, as shown in the exemplary embodiment of FIG. 32, an actuation element support 1000 may include a first flexible tube 1002 and a second flexible tube 1004 coaxial to one another, with one or more actuation elements 1010 extending through support 1000. Although only two coaxial tubes 1002, 1004 are depicted in the exemplary embodiment of FIG. 36, support 1000 may include other numbers of coaxial tubes, such as, for example, three, four, or more flexible coaxial tubes. Flexible tubes 1002, 1004 may be flexible due to removal of material from the tubes 1002, 1004, such as via cutting grooves or slits in tubes 1002, 1004 to provide areas of weakness that permit tubes 1002, 1004 to flex, according to an exemplary embodiment. According to an exemplary embodiment, tubes 1002, 1004 may be solid wound springs, which are useful for compression loads, with would filaments, which are useful for tensile loads.

According to another exemplary embodiment, a flexible shaft for supporting an actuation member may include multiple layers of wound filaments connected together. For example, instead of including the compression member 610 of the exemplary embodiment of FIG. 31, a flexible shaft may include a plurality of tension members 614 connected together, such as by weaving tension members 614 together. According to an exemplary embodiment, an actuation element support may be a flexible shaft formed by a tube with portions removed, such as via, for example, cutting the tube in one or more locations, to enhance the flexibility of the tube. The tube may be made of, for example, stainless steel, a thermoplastic, or other material one skilled in the art is familiar with.

The exemplary embodiments and methods described herein have been described as being utilized with surgical instruments for teleoperated surgical systems. However, the exemplary embodiments and methods described herein may be used with other surgical devices, such as laparoscopic instruments and other hand held instruments. Further, the exemplary embodiments and methods may be employed in other application that use remotely actuatable wrist or multiple joint structures, such as to remotely position an object attached to the wrist or joint structures.

By providing surgical instruments with an actuation element configured to substantially conserve its length when the surgical instrument is bent, the actuation element may be permitted to actuate a component of the instrument without substantial interference from a change in its length and the surgical instrument may have a simplified design that is relatively easy to manufacture.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical instrument, comprising:
   a shaft;
   a wrist coupled to a first end portion of the shaft, the wrist comprising a first joint and a second joint, the first joint having a first bend axis, the second joint having a second bend axis, and the first and second bend axes extending in different directions;
   an end effector coupled to the wrist; and
   an actuation element that extends along the shaft and the wrist;
   wherein the actuation element follows a twisted path along at least a portion of the wrist; and
   wherein the twisted path has an angular extent of less than 360 degrees along an entire length of the wrist.

2. The surgical instrument of claim 1, further comprising a transmission mechanism disposed at a second end portion of the shaft, wherein the transmission mechanism transmits drive forces along the actuation element.

3. The surgical instrument of claim 2, wherein the transmission mechanism transmits the drive forces along the actuation element to actuate the end effector.

4. The surgical instrument of claim 2, wherein the transmission mechanism transmits the drive forces along the actuation element to actuate the wrist.

5. The surgical instrument of claim 1, wherein an axis about which the twisted path twists is a longitudinal centerline of the wrist.

6. The surgical instrument of claim 1, wherein an axis about which the twisted path twists is radially offset from a longitudinal centerline of the wrist.

7. The surgical instrument of claim 1, wherein the first and second bend axes are orthogonal to one another.

8. The surgical instrument of claim 1, wherein the twisted path of the actuation element has an angular extent of 90 degrees across each of the first joint and the second joint of the wrist.

9. The surgical instrument of claim 1, wherein the actuation element is length conservative during bending for each of the first joint and the second joint of the wrist.

10. The surgical instrument of claim 1, wherein an angular extent of the twisted path across the first joint differs from an angular extent of the twisted path across the second joint.

11. The surgical instrument of claim 1, wherein the actuation element is length conservative across a combination of the first joint of the wrist and the second joint of the wrist but is not length conservative across each of the first joint or the second joint.

12. The surgical instrument of claim 1;
    wherein the wrist further comprises a third joint;
    wherein the actuation element is length conservative across the first joint of the wrist; and
    wherein the actuation element is length conservative across a combination of the second joint of the wrist and the third joint of the wrist but is not length conservative across each of the second joint and the third joint.

13. The surgical instrument of claim 1,
    wherein the wrist further comprises a third joint;
    wherein the actuation element is length conservative across the first joint of the wrist without following a twisted path along the first joint of the wrist; and
    wherein the actuation element is length conservative across a combination of the second joint of the wrist and the third joint of the wrist but not length conservative individually over the second joint or the third joint.

14. The surgical instrument of claim 13, wherein the actuation element follows a straight path across the first joint and is aligned with a bending axis of the first joint.

15. The surgical instrument of claim 13;
    wherein the actuation element follows the twisted path across the second joint and the third joint; and
    wherein the twisted path across the second joint and the third joint has an angular extent of 180 degrees.

16. The surgical instrument of claim 1:
    wherein the actuation element follows the twisted path across each of the first and second joints of the wrist; and
    wherein the actuation element is length conservative across each of the first and second joints of the wrist.

17. The surgical instrument of claim 16, wherein the twisted path has an angular extent of 240 degrees about a longitudinal centerline of the wrist and along the entire length of the wrist.

18. The surgical instrument of claim 1:
    wherein the second joint is adjacent to the first joint;
    wherein the wrist further comprises a third joint adjacent to the second joint and a fourth joint adjacent to the third joint;
    wherein the first bend axis of the first joint extends along a first direction;
    wherein the second bend axis of the second joint extends along a second direction different from the first direction;
    wherein the third joint has a third bend axis extending along the second direction; and
    wherein the fourth joint has a fourth bend axis extending along the first direction.

19. The surgical instrument of claim 1, further comprising:
    a second actuation element extending along the shaft and the wrist;
    wherein the second actuation element follows a second twisted path along at least a portion of the wrist; and
    wherein the twisted path of the actuation element and the second twisted path of the second actuation element are parallel to each other.

20. The surgical instrument of claim 1, further comprising:
    an actuation element support structure comprising at least one lumen defining the twisted path;

wherein the actuation element extends through the lumen of the actuation element support structure.

21. The surgical instrument of claim 20, wherein the actuation element support structure has a single-piece construction.

22. The surgical instrument of claim 20, wherein the actuation element support structure comprises one or more areas of material weakness relative to other areas of the actuation element support structure lacking one or more areas of material weakness.

23. The surgical instrument of claim 20:
wherein the actuation element support structure comprises separate links;
wherein each of the separate links comprises a passage that receives the actuation element; and
wherein the passages of the separate links are positioned at differing angular positions about a longitudinal centerline of the wrist.

24. The surgical instrument of claim 20, wherein the actuation element support structure comprises a compression member that resists compressive force and a tension member that resists tensile force.

25. The surgical instrument of claim 20, wherein the actuation element support structure comprises a plurality of flexible coaxial tubes.

26. The surgical instrument of claim 1, wherein the actuation element comprises a rigid structure.

27. The surgical instrument of claim 26, wherein the rigid structure is a metal cylinder.

28. The surgical instrument of claim 26, wherein the actuation element comprises a coating disposed adjacent to the rigid structure.

29. The surgical instrument of claim 1, wherein the wrist comprises a plurality of connected links.

30. A support structure for an actuation element of a surgical instrument, comprising:
a passage radially offset from a central longitudinal axis of the support structure,
wherein the passage comprises a first end and a second end and defines a twisted path from the first end of the passage to the second end of the passage about the central longitudinal axis of the support structure; and
wherein the passage has an angular extent of less than 360 degrees from the first end of the passage to the second end of the passage.

31. The support structure of claim 30, further comprising:
a second passage radially offset from the central longitudinal axis of the support structure;
wherein the second passage comprises a first end and a second end and defines a second twisted path from the first end of the second passage to the second end of the second passage about the central longitudinal axis of the support structure; and
wherein the second passage has an angular extent of less than 360 degrees from the first end of the second passage to the second end of the second passage.

32. The support structure of claim 30, further comprising one or more portions having areas of material weakness relative to other portions.

33. The support structure of claim 30, wherein the support structure has a single-piece construction.

* * * * *